(12) United States Patent
Matsushima

(10) Patent No.: US 10,376,245 B2
(45) Date of Patent: Aug. 13, 2019

(54) INFORMATION PROCESSING DEVICE, INFORMATION PROCESSING METHOD, AND INFORMATION PROCESSING PROGRAM

(71) Applicant: Rakuten, Inc., Tokyo (JP)

(72) Inventor: Katsuhito Matsushima, Tokyo (JP)

(73) Assignee: Rakuten, Inc., Setagaya-ku, Tokyo (JP)

( * ) Notice: Subject to any disclaimer, the term of this patent is extended or adjusted under 35 U.S.C. 154(b) by 466 days.

(21) Appl. No.: 15/037,756

(22) PCT Filed: Nov. 28, 2013

(86) PCT No.: PCT/JP2013/082002
§ 371 (c)(1),
(2) Date: May 19, 2016

(87) PCT Pub. No.: WO2015/079526
PCT Pub. Date: Jun. 4, 2015

(65) Prior Publication Data
US 2016/0296210 A1 Oct. 13, 2016

(51) Int. Cl.
*A61B 5/00* (2006.01)
*A61B 10/00* (2006.01)
*G16H 10/60* (2018.01)

(52) U.S. Cl.
CPC ......... *A61B 10/0012* (2013.01); *G16H 10/60* (2018.01); *A61B 2010/0019* (2013.01)

(58) Field of Classification Search
CPC ........ A61B 10/0012; A61B 2010/0019; A61B 2010/0029; G16H 10/60
See application file for complete search history.

(56) References Cited

U.S. PATENT DOCUMENTS 9,155,523 B2 * 10/2015 James ................. A61B 10/0012
9,592,033 B2 * 3/2017 Toriumi .................. A61B 5/746

FOREIGN PATENT DOCUMENTS

JP 2012-32337 A 2/2012

OTHER PUBLICATIONS

International Search Report of PCT/JP2013/082002, dated Jan. 28, 2014. [PCT/ISA/210].

* cited by examiner

*Primary Examiner* — Max F Hindenburg
(74) *Attorney, Agent, or Firm* — Sughrue Mion, PLLC

(57) ABSTRACT

It is an object to estimate an ovulation date using less menstrual cycles of body temperatures while preventing decrease in estimation accuracy. An information processing device obtains the equation of a function that approximates the relationship between body temperature data and dates. The information processing device determines a low-temperature-phase reference body temperature, based on a plurality of days of body temperature data identified based on the date corresponding to a local minimum value in the function, and determines a high-temperature-phase reference body temperature, based on a plurality of days of body temperature data identified based on the date corresponding to a local maximum value in the function. Then, the information processing device estimates an ovulation date in the current menstrual cycle, based on a determination reference body temperature set at a value between the low-temperature-phase reference body temperature and the high-temperature-phase reference body temperature and on measurement data.

12 Claims, 22 Drawing Sheets

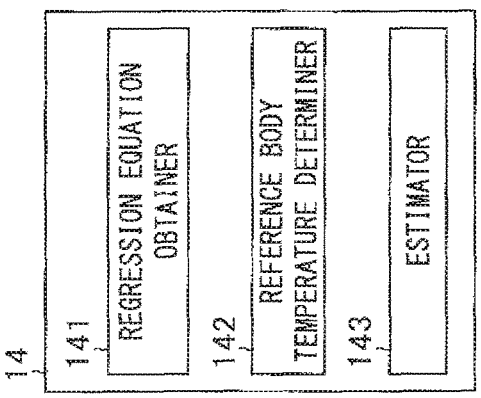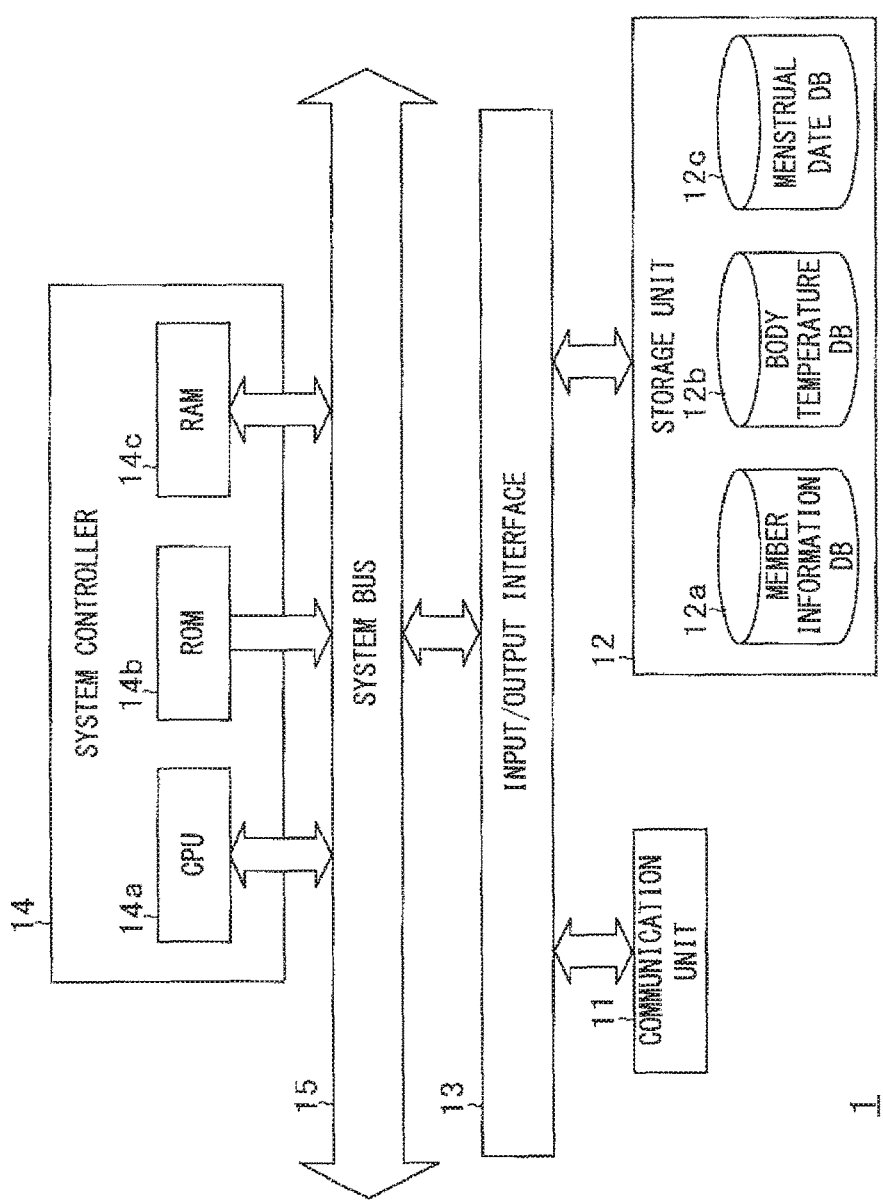

FIG.3A
MEMBER INFORMATION DB 12a

| USER ID |
| --- |
| PASSWORD |
| NICKNAME |
| NAME |
| BIRTH DATE |
| GENDER |
| ZIP CODE |
| ADDRESS |
| TELEPHONE NUMBER |
| E-MAIL ADDRESS |
| ... |

FIG.3B
BODY TEMPERATURE DB 12b

| USER ID |
| --- |
| MEASUREMENT DATE |
| MEASURED BODY TEMPERATURE |

FIG.3C
MENSTRUAL DATE DB 12c

| USER ID |
| --- |
| MENSTRUAL DATE |

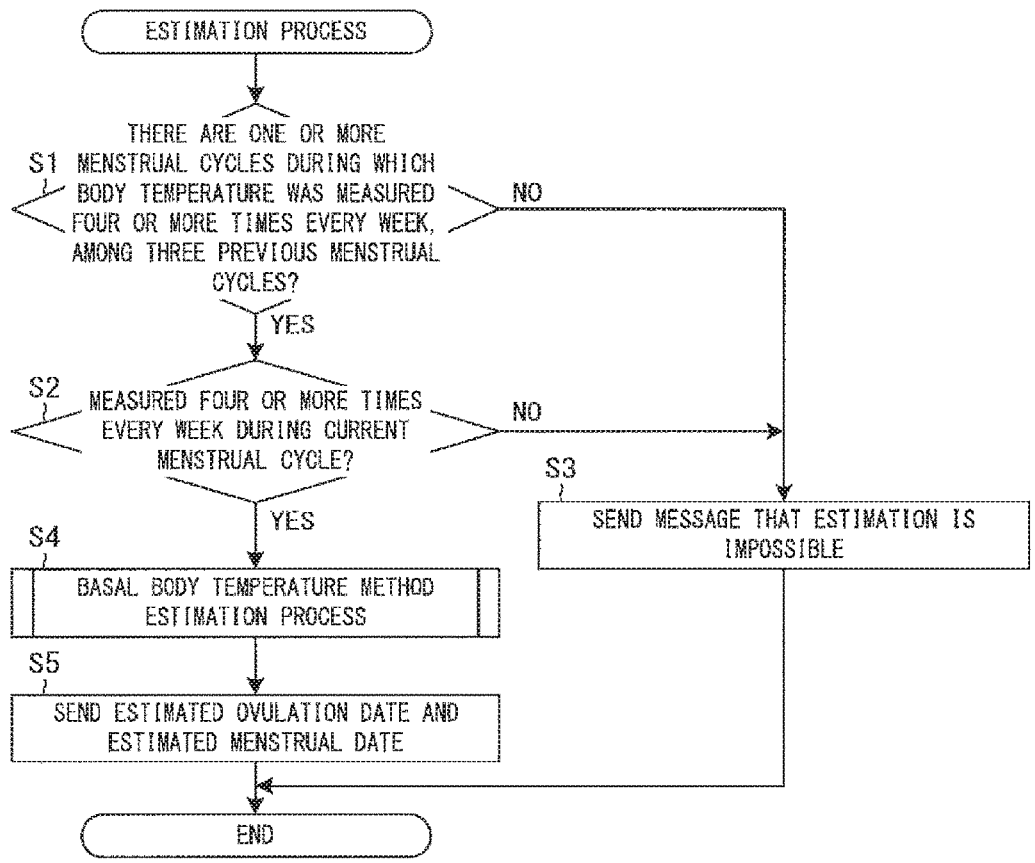

FIG.7

| TODAY'S BODY TEMPERATURE | ESTIMATED OVULATION DATE |
| --- | --- |
| 36.27°C | 2/23 (SAT) — D1 |

| NEXT ESTIMATED MENSTRUAL DATE | POSSIBILITY OF PREGNANCY |
| --- | --- |
| D2 — 3/9 (SAT) 19 DAYS LATER | MEDIUM |

| BEAUTIFULNESS | ○●●●● |
| --- | --- |
| SKIN | MOIST SKIN |
| MOOD | POSITIVE AND HAPPY |
| DIET | CRUCIAL MOMENT |

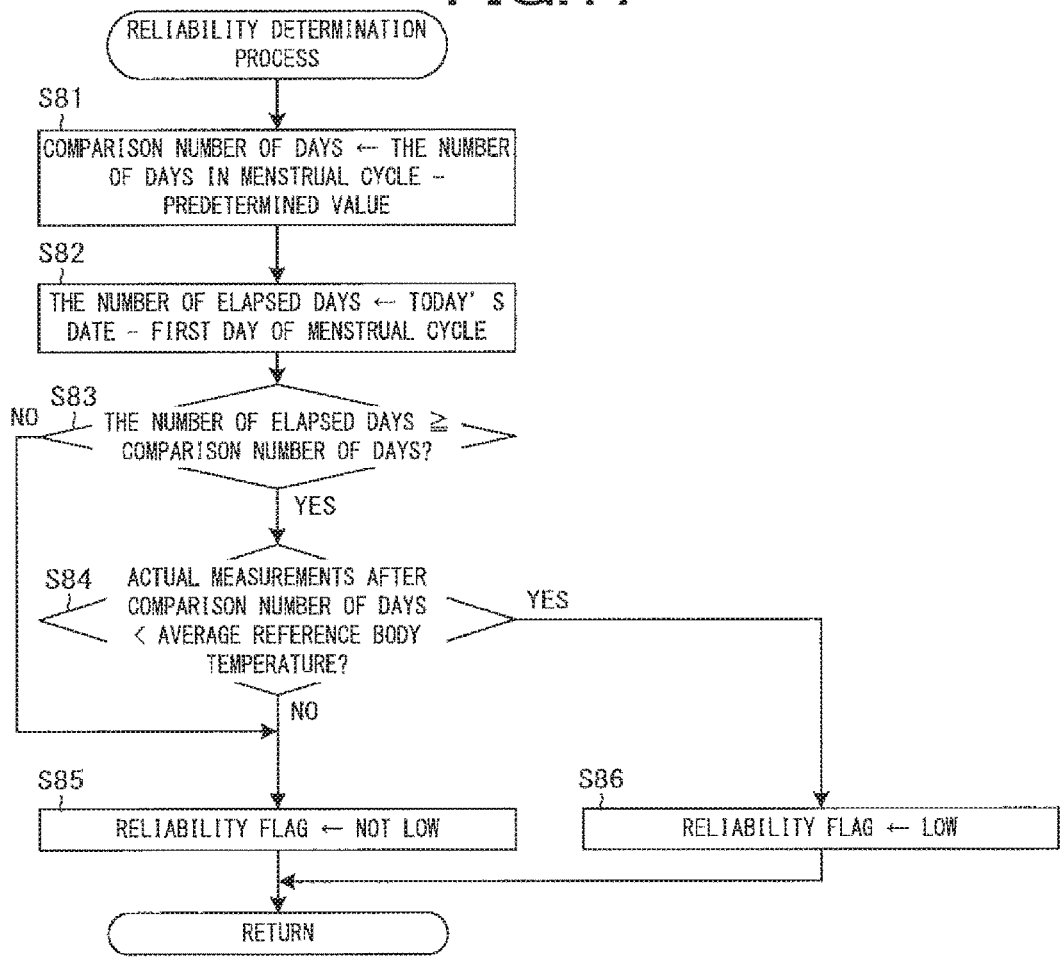

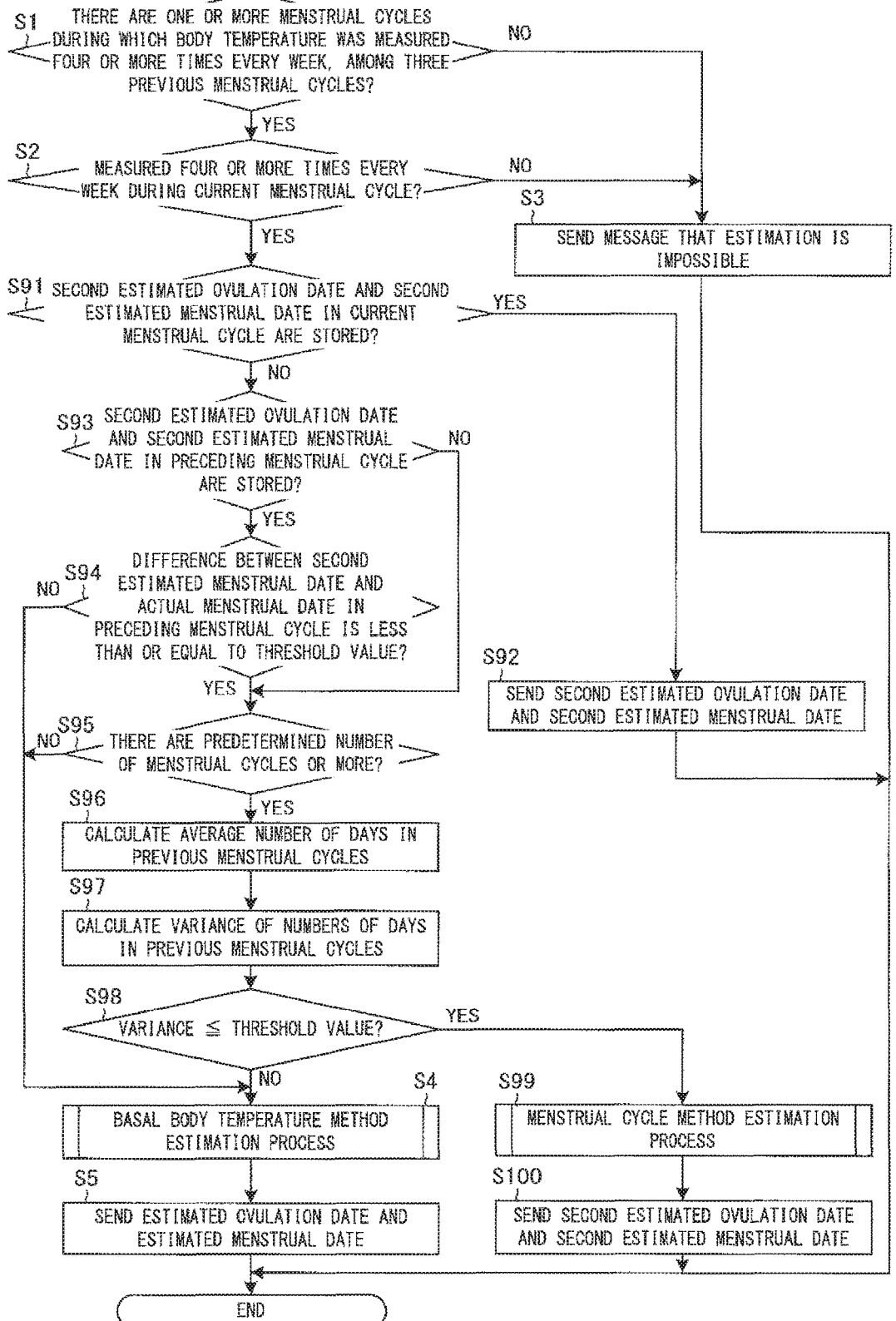

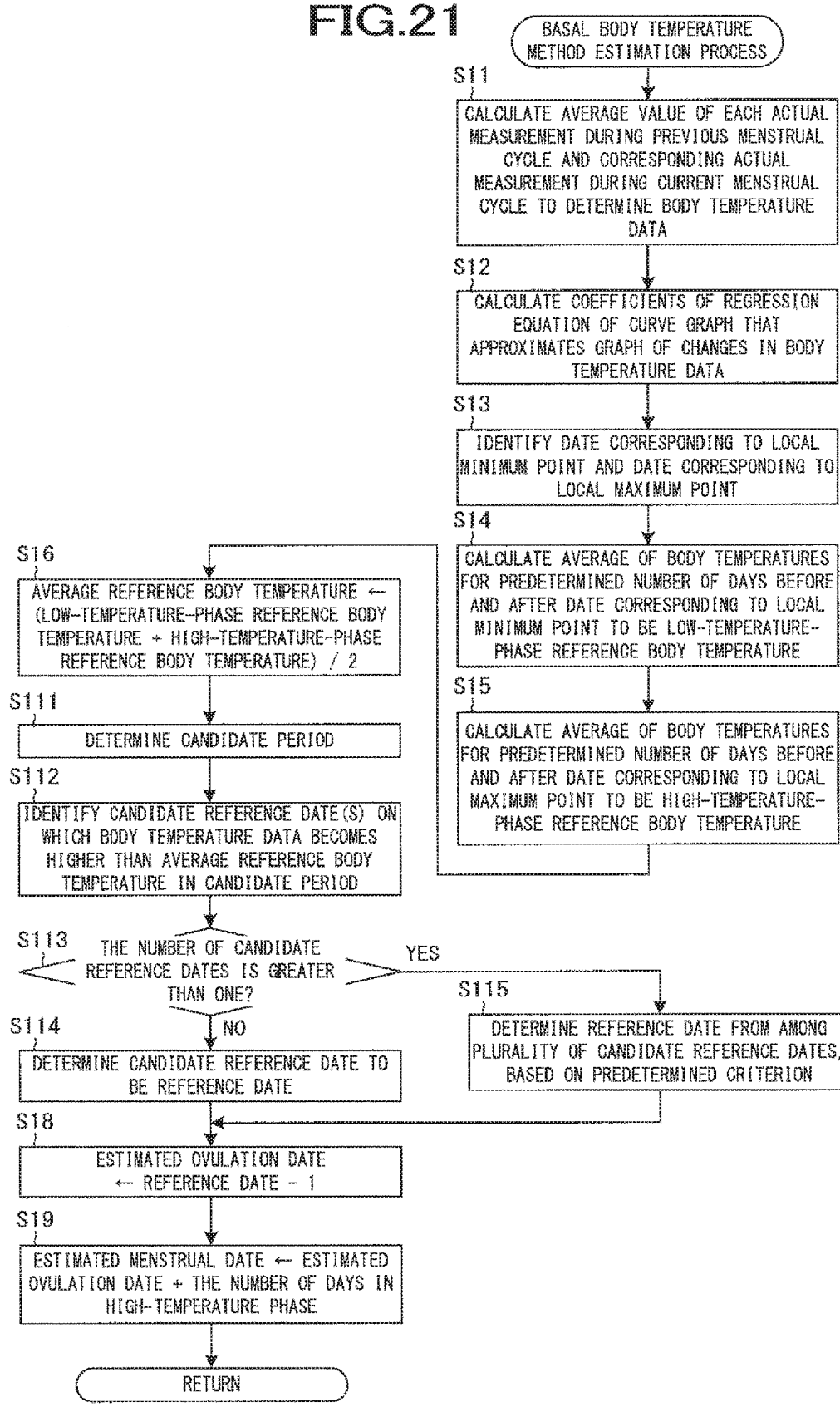

INFORMATION PROCESSING DEVICE, INFORMATION PROCESSING METHOD, AND INFORMATION PROCESSING PROGRAM

CROSS REFERENCE TO RELATED APPLICATIONS

This application is a National Stage of International Application No. PCT/JP2013/082002 filed Nov. 28, 2013, the contents of all of which are incorporated herein by reference in their entirety.

TECHNICAL FIELD

The present invention relates to techniques for estimating an ovulation date, based on measured body temperatures.

BACKGROUND ART

For example, Patent Literature 1 discloses that when measurements of body temperature have been obtained for over a predetermined number of menstrual cycles, an ovulation date and menstrual dates are estimated based on measurements determined to be valid among the obtained measurements, and that when the number of menstrual cycles during which measurements have been obtained is less than the predetermined number, the obtained measurements are regarded as valid and used to perform the estimation.

CITATION LIST

Patent Literature

Patent Literature 1: JP 2012-032337 A

SUMMARY OF INVENTION

Technical Problem

However, to ensure estimation accuracy of an ovulation date and menstrual dates, the technique described in Patent Literature 1 requires measurements of body temperature that have been obtained for over the predetermined number of menstrual cycles.

In view of the above point, it is an object of the present invention to provide an information processing device, an information processing method, and an information processing program that estimate an ovulation date using less menstrual cycles of body temperatures while preventing decrease in estimation accuracy.

Solution to Problem

To solve the above problem, the invention according to claim 1 is an information processing device that includes obtaining means, determining means, and estimating means. The obtaining means obtains the equation of a function of date. The function approximates the relationship between body temperature data and dates and has a local minimum value and a local maximum value. The body temperature data is obtained based on actual measurements during at least one menstrual cycle. The determining means determines a low-temperature-phase reference body temperature, based on a plurality of days of body temperature data that are identified based on the date corresponding to the local minimum value in the function defined by the equation obtained by the obtaining means. The determining means determines a high-temperature-phase reference body temperature, based on a plurality of days of body temperature data that are identified based on the date corresponding to the local maximum value in the function. The estimating means estimates an ovulation date in the current menstrual cycle, based on a determination reference body temperature set at a value between the low-temperature-phase reference body temperature and the high-temperature-phase reference body temperature that are determined by the determining means and on measurement data including a plurality of days of the body temperature data associated with dates.

According to this invention, an information processing device obtains the equation of a function of date that approximates the relationship between body temperature data and dates and that has a local minimum value and a local maximum value. Thus, the information processing device can respectively identify the dates corresponding to the local minimum value and the local maximum value as dates included in a low-temperature phase and a high-temperature phase, while reducing the effect of noise in actual measurements. Then, the information processing device estimates an ovulation date, based on a low-temperature-phase reference body temperature and a high-temperature-phase reference body temperature. Consequently, the effect of noise in actual measurements is reduced, and it becomes possible to estimate an ovulation date using less menstrual cycles of body temperatures while preventing decrease in estimation accuracy.

The invention according to claim 2 is the information processing device according to claim 1 in which the estimating means identifies a date on which body temperature data becomes higher than the determination reference body temperature as a reference date, in a period included in the measurement data, and estimates the ovulation date, based on the reference date.

According to this invention, when the body temperature actually measured rises is identified. Thus, an ovulation date is correctly estimated.

The invention according to claim 3 is the information processing device according to claim 1 in which when there are a plurality of candidate dates on which the body temperature data is higher than the determination reference body temperature and whose preceding day's body temperature data is lower than the determination reference body temperature, during the period from a predetermined number of days after the date corresponding to the local minimum value to a predetermined number of days before the date corresponding to the local maximum value, the estimating means determines one candidate date to be a reference date, based on a predetermined criterion, and estimates the ovulation date, based on the reference date.

According to this invention, a reference date is properly identified even if measurement data includes any noise. Consequently, estimation accuracy is improved.

The invention according to claim 4 is the information processing device according to claim 1 in which the estimating means identifies a date on which body temperature calculated by using the equation obtained by the obtaining means becomes higher than the determination reference body temperature as a reference date, and estimates the ovulation date, based on the reference date.

According to this invention, an ovulation date is estimated base on the function with less effect of noise. Consequently, decrease in estimation accuracy is prevented.

The invention according to claim 5 is the information processing device according to any one of claims 1 to 4 in which the obtaining means obtains the equation of the function that approximates the relationship between body temperature data obtained based on actual measurements during at least one previous menstrual cycle and on actual measurements during the current menstrual cycle and dates.

According to this invention, the information processing device obtains the equation of the function also using the actual measurements during the current menstrual cycle. This allows changes in body temperature during the current menstrual cycle to be reflected in the function. Consequently, estimation accuracy is improved.

The invention according to claim 6 is the information processing device according to claim 5 in which the obtaining means assigns a higher weight to the actual measurements during the current menstrual cycle than to the actual measurements during the previous menstrual cycle, calculates a weighted average of each actual measurement during the previous menstrual cycle and a corresponding actual measurement during the current menstrual cycle, and obtains the equation of the function that approximates a relationship between body temperature data including the weighted averages and dates.

According to this invention, the information processing device obtains the equation of a curve graph while placing more weight on the actual measurements during the current menstrual cycle than on the actual measurements during the previous menstrual cycle. This allows changes in body temperature during the current menstrual cycle to be further reflected in the function. Consequently, estimation accuracy is improved.

The invention according to claim 7 is the information processing device according to any one of claims 1 to 6 further including the second obtaining means, the second determining means, the second estimating means, and the identifying means. The second obtaining means obtains a plurality of equations of mutually different degrees of a plurality of functions. Each function approximates the relationship between body temperature data and dates and has a local minimum value and a local maximum value. The body temperature data is obtained based on actual measurements during at least one previous menstrual cycle. For each of the equations obtained by the second obtaining means, the second determining means determines a low-temperature-phase reference body temperature, based on a plurality of days of actual measurements that are identified based on the date corresponding to the local minimum value, and determines a high-temperature-phase reference body temperature, based on a plurality of days of actual measurements that are identified based on the date corresponding to the local maximum value. For each of the equations obtained by the second obtaining means, the second estimating means estimates a menstrual date in the at least one previous menstrual cycle, based on a body temperature set at a value between the low-temperature-phase reference body temperature and the high-temperature-phase reference body temperature that are determined by the second determining means and on a plurality of days of the actual measurements. The identifying means identifies the degree of an equation that minimizes the difference between a menstrual date estimated by the second estimating means and an actual menstrual date, from among the plurality of equations obtained by the second obtaining means. The obtaining means obtains the equation of the degree identified by the identifying means.

According to this invention, the information processing device determines the degree that maximizes estimation accuracy of the menstrual date in the previous menstrual cycle, among the plurality of degrees, to be the degree of the equation for estimating an ovulation date in the current menstrual cycle. Consequently, estimation accuracy is improved.

The invention according to claim 8 is the information processing device according to any one of claims 1 to 7 in which the obtaining means obtains the equation of the function that approximates the relationship between body temperature data and dates, and the body temperature data is obtained based on actual measurements during at least one previous menstrual cycle and on actual measurements during the current menstrual cycle. The information processing device further includes determination means. The determination means determines whether the reliability of the actual measurements during the current menstrual cycle meets a predetermined requirement, based on the actual measurements during the at least one previous menstrual cycle. If the determination means determines that the reliability does not meet the predetermined requirement, the estimating means estimates the ovulation date based on information about the at least one previous menstrual cycle, without using either the low-temperature-phase reference body temperature or the high-temperature-phase reference body temperature that is determined based on the actual measurements during the current menstrual cycle.

According to this invention, when the reliability of actual measurements during the current menstrual cycle is low, the information processing device does not use the actual measurements during the current menstrual cycle. Consequently, decrease in estimation accuracy due to using actual measurements during the current menstrual cycle is prevented.

The invention according to claim 9 is the information processing device according to any one of claims 1 to 8 in which when the difference between a plurality of previous menstrual cycles and the average of the plurality of menstrual cycles is less than or equal to a predetermined value, the estimating means estimates the ovulation date and the next menstrual date based on the average of the plurality of menstrual cycles, without using either the low-temperature-phase reference body temperature or the low-temperature-phase reference body temperature.

According to this invention, when the previous menstrual cycles were stable, the information processing device improves estimation accuracy, even without using the equation of a curve graph that approximates a graph of changes in body temperature.

The invention according to claim 10 is the information processing device according to claim 9 in which when the difference between a menstrual date estimated based on the average of the plurality of menstrual cycles and an actual menstrual date is greater than a predetermined value, the estimating means estimates an ovulation date in the current menstrual cycle, based on the low-temperature-phase reference body temperature and the high-temperature-phase reference body temperature that are determined by using the equation of the function that approximates the relationship between body temperature data and dates, and the body temperature data is obtained based on actual measurements during at least one previous menstrual cycle and actual measurements during the current menstrual cycle.

According to this invention, when the difference between an actual menstrual date in the preceding menstrual cycle and a menstrual date estimated based on an average of the previous menstrual cycles is large, the information processing device estimates an ovulation date in the current menstrual cycle by using the equation of a curve graph that approximates a graph of changes in body temperature, without using the average of previous menstrual cycles. Consequently, when the preceding menstrual cycle was irregular, decrease in estimation accuracy due to using the average of previous menstrual cycles is prevented.

The invention according to claim 11 is an information processing method performed by a computer. The method includes the following steps. The equation of a function of date is obtained. The function approximates the relationship between body temperature data and dates and has a local minimum value and a local maximum value. The body temperature data is obtained based on actual measurements during at least one menstrual cycle. A low-temperature-phase reference body temperature is determined based on a plurality of days of body temperature data that are identified based on the date corresponding to the local minimum value in the function defined by the obtained equation. A high-temperature-phase reference body temperature is determined based on a plurality of days of body temperature data that are identified based on the date corresponding to the local maximum value in the function. An ovulation date in the current menstrual cycle is estimated based on a determination reference body temperature set at a value between the determined low-temperature-phase reference body temperature and the determined high-temperature-phase reference body temperature and on measurement data including a plurality of days of the body temperature data associated with dates.

The invention according to claim 12 is an information processing program that causes a computer to function as obtaining means, determining means, and estimating means. The obtaining means obtains the equation of a function of date. The function approximates the relationship between body temperature data and dates and has a local minimum value and a local maximum value. The body temperature data is obtained based on actual measurements during at least one menstrual cycle. The determining means determines a low-temperature-phase reference body temperature, based on a plurality of days of body temperature data that are identified based on the date corresponding to the local minimum value in the function defined by the equation obtained by the obtaining means. The determining means determines a high-temperature-phase reference body temperature, based on a plurality of days of body temperature data that are identified based on the date corresponding to the local maximum value in the function. The estimating means estimates an ovulation date in the current menstrual cycle, based on a determination reference body temperature set at a value between the low-temperature-phase reference body temperature and the high-temperature-phase reference body temperature that are determined by the determining means and on measurement data including a plurality of days of the body temperature data associated with dates.

Advantageous Effects of Invention

According to the present invention, an information processing device obtains the equation of a function of date that approximates the relationship between body temperature data and dates and that has a local minimum value and a local maximum value. Thus, the information processing device can respectively identify the dates corresponding to the local minimum value and the local maximum value as dates included in a low-temperature phase and a high-temperature phase, while reducing the effect of noise in actual measurements. Then, the information processing device estimates an ovulation date, based on a low-temperature-phase reference body temperature and a high-temperature-phase reference body temperature. Consequently, the effect of noise in actual measurements is reduced, and it becomes possible to estimate an ovulation date using less menstrual cycles of body temperatures while preventing decrease in estimation accuracy.

BRIEF DESCRIPTION OF DRAWINGS

FIG. 2A is a block diagram schematically showing an example configuration of an information processing server 1 according to an embodiment.

FIG. 2B is a diagram showing example functional blocks of a system controller 14 according to an embodiment.

FIG. 3A is a diagram showing example contents stored in a member information DB 12a.

FIG. 3B is a diagram showing example contents stored in a body temperature DB 12b.

FIG. 3C is a diagram showing example contents stored in a menstrual date DB 12c.

FIG. 6 is a flowchart showing an example process of an estimation process in the system controller 14 of the information processing server 1 according to an embodiment.

FIG. 7 is a diagram showing an example screen display of an estimation result.

FIG. 17 is a flowchart showing an example process of the reliability determination process in the system controller 14 of the information processing server 1 according to an embodiment.

FIG. 18 is a flowchart showing an example process of the estimation process in the system controller 14 of the information processing server 1 according to an embodiment.

FIG. 21 is a flowchart showing an example process of the basal body temperature method estimation process in the system controller 14 of the information processing server 1 according to this embodiment.

DESCRIPTION OF EMBODIMENTS

The following describes embodiments of the present invention in detail with reference to the drawings. The embodiments described below are embodiments in which the present invention is applied to an information processing system.

Figure 1:
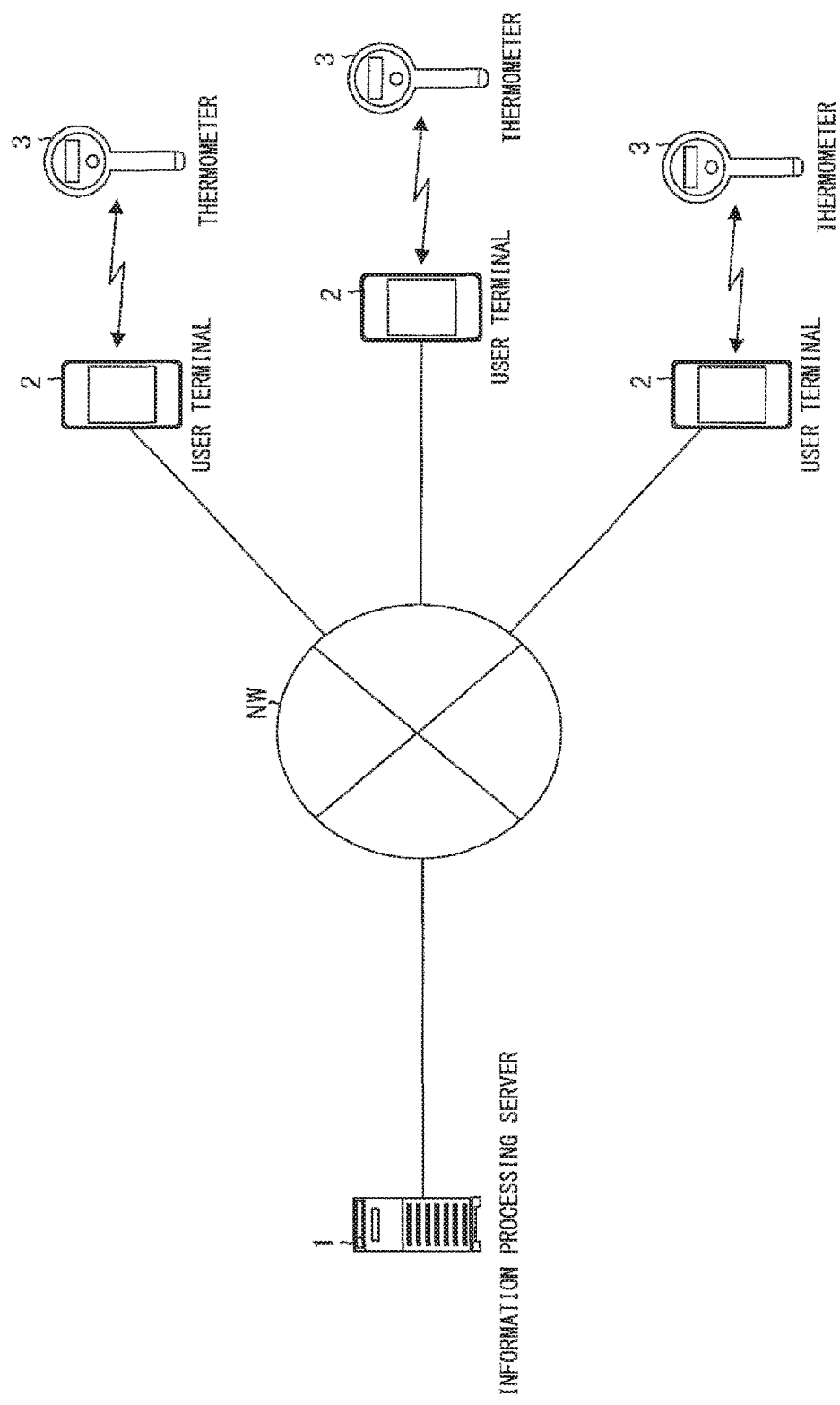
FIG. 1 is a diagram schematically showing an example configuration of an information processing system S according to an embodiment.

1. First Embodiment 1-1. Configuration and Functional Overview of Information Processing System First, a configuration and a functional overview of an information processing system S according to this embodiment are described with reference to FIGS. 1 to 4B. FIG. 1 is a diagram schematically showing an example configuration of the information processing system S according to this embodiment.

As shown in FIG. 1, the information processing system S includes an information processing server 1, a plurality of user terminals 2, and a plurality of thermometers 3. The information processing server 1 can exchange data with each user terminal 2 over a network NW using communication protocols, such as TCP/IP. The network NW includes, for example, the Internet, a dedicated communication line (e.g., community antenna television (CATV) line), a mobile communication network (including base stations), and a gateway.

The information processing server 1 is a server device that delivers information about the health of a woman to the user terminal 2. The information processing server 1 obtains, from the user terminal 2, information about, for example, the user's basal body temperatures and menstrual dates. The information processing server 1 then estimates an ovulation date and the next menstrual date of the user, based on the obtained information.

The user terminal 2 is a terminal device of a user who uses the information processing system S. The user terminal 2 may be, for example, a smartphone, a tablet computer, a personal digital assistant (PDA), a mobile phone, or a personal computer. The user terminal 2 sends basal body temperatures measured by the thermometer 3 to the information processing server 1. The user terminal 2 also sends actual menstrual dates entered by the user to the information processing server 1. The user terminal 2 then displays information about an ovulation date and a menstrual date that are estimated by the information processing server 1.

The thermometer 3 is a digital thermometer that measures the basal body temperature of the user. The thermometer 3 sends the measured body temperature to the user terminal 2, for, example, via near field communication. The user may manually enter the body temperature measured by a thermometer into the user terminal 2.

The user takes her body temperature with the thermometer 3 on a daily basis. An actually measured body temperature is referred to as an actual measurement. When the user enters an actual menstrual date, a menstrual cycle is identified. The menstrual cycle is the period from the preceding menstrual date to the day before the next menstrual date. When menstruation lasts two or more days, the information processing server 1 determines the first day of the menstruation to be a menstrual date used to identify the menstrual cycle. The information processing server 1 estimates an ovulation date, based on body temperatures measured for menstrual cycle(s). The information processing server 1 then estimates the next menstrual date, based on the estimated ovulation date. The ovulation date thus estimated is referred to as an estimated ovulation date, and the menstrual date thus estimated is referred to as an estimated menstrual date.

To estimate an ovulation date from less menstrual cycles of actual measurements while preventing decrease in estimation accuracy, the information processing server 1 performs the estimation by using the equation (regression equation) of a function that approximates changes in body temperature, using regression analysis. This estimation method is referred to as a basal body temperature method. How to estimate an ovulation date is described in detail later.

1-2. Configuration of Information Processing Server

The following describes a configuration of the information processing server 1 with reference to FIGS. 2A to 3C.

FIG. 2A is a block diagram schematically showing an example configuration of the information processing server 1 according to this embodiment. As shown in FIG. 2A, the information processing server 1 includes a communication unit 11, a storage unit 12, an input/output interface 13, and a system controller 14. The system controller 14 and the input/output interface 13 are connected via a system bus 15.

The communication unit 11 connects to the network NW and controls the state of communications with, for example, the user terminals 2.

The storage unit 12 includes, for example, hard disk drives. The storage unit 12 is an example of storage means. In this storage unit 12, a member information DB 12, a body temperature DB 12*b*, a menstrual date DB 12*c*, and other databases are created. "DB" is an abbreviation for database.

FIG. 3A is a diagram showing example contents stored in the member information DB 12*a*. The member information DB 12*a* stores user information about users who use the information processing system S. Specifically, the member information DB 12*a* stores, for each user, the user's user ID, password, nickname, name, birth date, gender, zip code, address, telephone number, e-mail address, and other user attributes in association with each other. The user ID is identification information of the user.

FIG. 3B is a diagram showing example contents stored in the body temperature DB 12b. The body temperature DB 12b stores information about actual measurements. Specifically, the body temperature DB 12b stores a user ID, a measurement date, and an actual measurement in association with each other. The user ID indicates a user who took her body temperature. The measurement date indicates the date on which the body temperature was measured. For example, the system controller 14 receives, from a user terminal 2, a user ID of a user who uses the user terminal 2, a measurement date, and an actual measurement. Then, the system controller 14 stores the received information in the body temperature DB 12b.

FIG. 3C is a diagram showing example contents stored in the menstrual date DB 12c. The menstrual date DB 12c stores information about menstrual dates. Specifically, the menstrual date DB 12c stores a user ID and a menstrual date in association with each other. The user ID indicates the user who entered the menstrual date. For example, the system controller 14 receives, from a user terminal 2, a user ID of a user who uses the user terminal 2 and a menstrual date that the user entered. Then, the system controller 14 stores the received information in the menstrual date DB 12c.

The following describes other information stored in the storage unit 12. The storage unit 12 stores various data, such as HTML documents, extensible markup language (XML) documents, image data, text data, and electronic documents, for displaying web pages. The storage unit 12 also stores various setting values, threshold values, constants, and the like.

The storage unit 12 also stores various programs, such as an operating system, a World Wide Web (WWW) server program, a database management system (DBMS), and an estimation process program. The estimation process program is a program for estimating an ovulation date and a menstrual date. The estimation process program is an example of an information processing program according to the present invention. The various programs may be available from, for example, another server device over the network NW, or may be recorded in a recording medium, such as an optical disk, and be read via a drive device. The estimation process program may be a program product.

The storage unit 12 also stores a terminal application program. The terminal application program is a program to be performed by the user terminal 2. The terminal application program is a program for sending information such as actual measurements and menstrual dates to the information processing server 1 and for displaying information such as an estimated ovulation date and an estimated menstrual date. The user terminal 2 downloads the terminal application program, for example, from the information processing server 1.

The input/output interface 13 performs interface processing between the communication unit 11 and the storage unit 12, and the system controller 14.

The system controller 14 includes, for example, a CPU 14a, a read only memory (ROM) 14b, and a random access memory (RAM) 14c. The CPU 14a is an example of a processor. The present invention can also be applied to various processors other than CPUs. The storage unit 12, the ROM 14b, and the RAM 14c are each an example of a memory. The present invention can also be applied to various memories other than hard disks, ROMs, and RAMs.

FIG. 2B is a diagram showing example functional blocks of the system controller 14 according to this embodiment. As shown in FIG. 2B, the estimation process program and other programs, which are read and executed by the CPU 14a, enable the system controller 14 to function as, for example, a regression equation obtainer 141, a reference body temperature determiner 142, and an estimator 143. The regression equation obtainer 141 is an example of obtaining means of the present invention. The reference body temperature determiner 142 is an example of determining means of the present invention. The estimator 143 is an example of estimating means of the present invention.

The regression equation obtainer 141 obtains the regression equation of a function that approximates the relationship between body temperature data and dates. The temperature data is obtained is obtained based on actual measurements during at least one menstrual cycle. In this embodiment, a curve graph is used as an example of the function. Specifically, the regression equation obtainer 141 obtains the regression equation of a curve graph that approximates a graph of changes in body temperature. When the body temperature is measured in the current menstrual cycle, the regression equation obtainer 141 can use actual measurements during the current menstrual cycle as well as actual measurements during previous menstrual cycle(s).

Figure 4A:
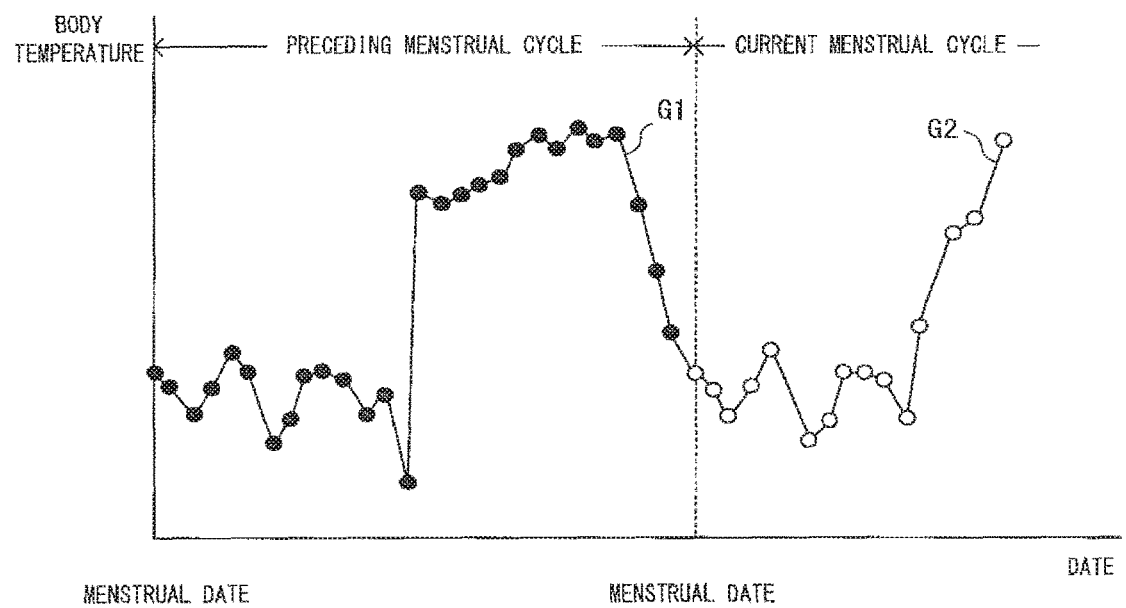
FIG. 4A is a graph showing example changes in actual measurement.
Figure 4B:
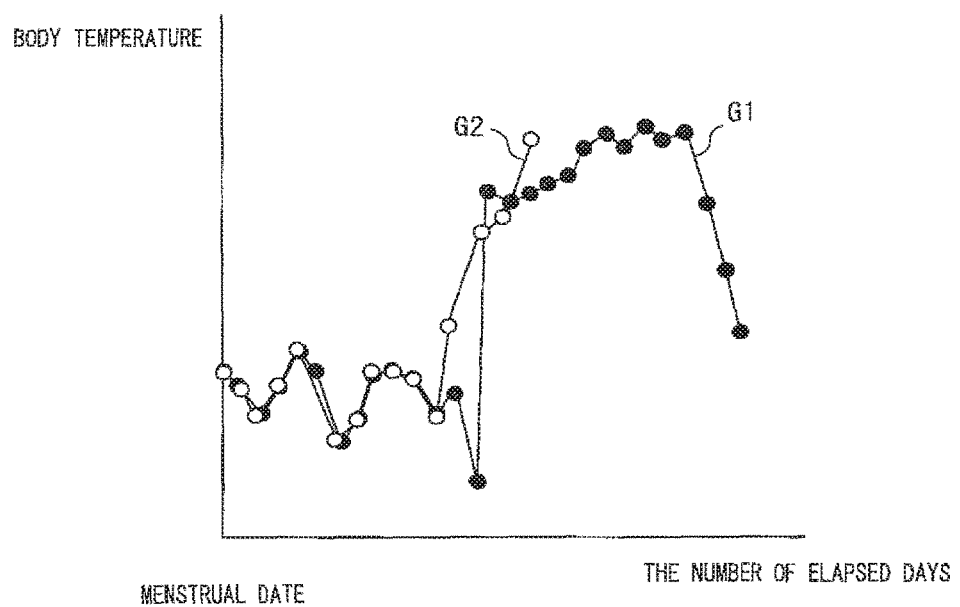
FIG. 4B is a diagram overlaying a graph G1 on a graph G2 so that the first day of the preceding menstrual cycle coincides with the first day of the current menstrual cycle.
Figure 5A:
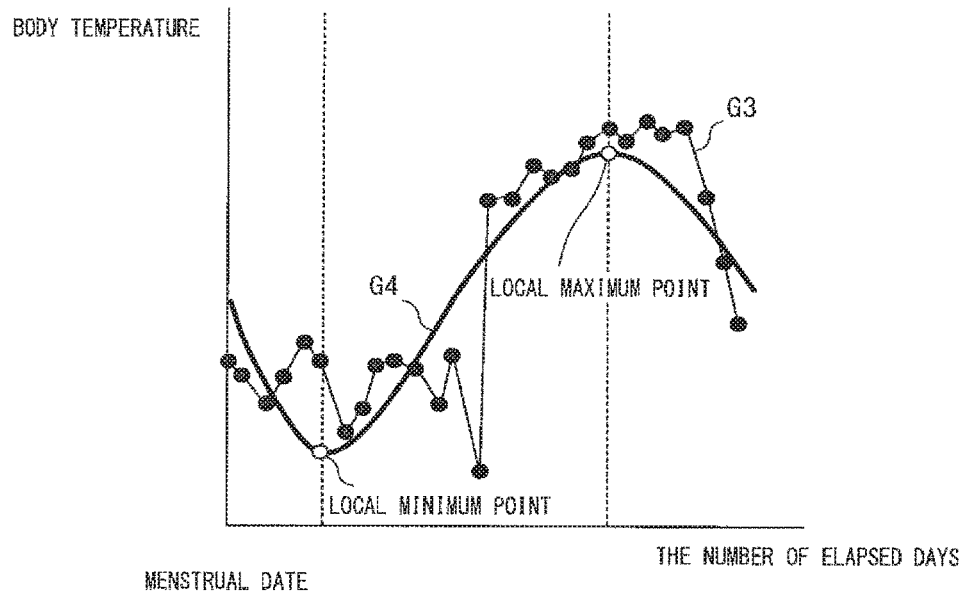
FIG. 5A is a graph showing example changes in body temperature data and an example result of regression analysis.

FIG. 4A is a graph showing example changes in actual measurement. FIG. 4A shows changes in actual measurement from the preceding menstrual cycle to the current menstrual cycle. The current time is within the current menstrual cycle, and thus the last day of the current menstrual cycle has not yet been fixed. The graph G1 shows changes in actual measurement during the preceding menstrual cycle, and the graph G2 shows changes in actual measurement during the current menstrual cycle. For example, assume that the regression equation obtainer 141 uses the actual measurements during the preceding menstrual cycle as actual measurements during a previous menstrual cycle. Based on the actual measurements, the regression equation obtainer 141 determines body temperatures indicating changes to be approximated. These body temperatures are referred to as body temperature data. The body temperature data is, for example, a representative value of actual measurements. For example, between the actual measurements during the previous menstrual cycle and the actual measurements during the current menstrual cycle, the regression equation obtainer 141 may calculate the average of each pair of actual measurements that were obtained the same number of days after the first day of the corresponding menstrual cycle to be body temperature data. For example, the regression equation obtainer 141 may calculate a simple average. If an actual measurement during one of the previous and current menstrual cycles was not obtained certain days after the corresponding first day, the regression equation obtainer 141 may determine an actual measurement during the other menstrual cycle directly to be body temperature data. FIG. 4B is a diagram overlaying the graph G1 on the graph G2 so that the first day of the preceding menstrual cycle coincides with the first day of the current menstrual cycle. FIG. 5A is a graph showing example changes in body temperature data and an example result of regression analysis. Overlaying the graph G1 on the graph G2 and taking the average of the graphs gives the graph G3 of changes in body temperature data as shown in FIG. 5A. The regression equation obtainer 141 associates the obtained body temperature data and the corresponding dates (the numbers of days since the menstrual date) with each other. The combination of the body temperature data and the dates that are associated with each other is referred to as measurement data.

The regression equation obtainer 141 obtains the regression equation of a function that approximates the relationship between the body temperature data and dates. At this time, the regression equation obtainer 141 obtains the regression equation of a function of date that has a local minimum value and a local maximum value. That is, the regression equation obtainer 141 obtains such a regression equation that the curve graph includes a local minimum value and a local maximum value within a menstrual cycle. Thus, the degree of the regression equation is three or more. For example, the degree may be preset. The regression equation may be, for example, the following polynomial, where x is the number of days since the first day of a menstrual cycle, y is body temperature, N is the degree, and a0 to aN are each the coefficient of the corresponding term.

$$y = a_0 + a_1 x^1 + a_2 x^2 + \ldots a_N x^N$$

The regression equation obtainer 141 obtains the regression equation by calculating the coefficient of each term. A menstrual cycle can be typically divided into a low-temperature phase and a high-temperature phase. The low-temperature phase is the period from the first day of the menstrual cycle to the ovulation date. The high-temperature phase is the period from the day after the ovulation date to the last day of the menstrual cycle. Usually, body temperature during the low-temperature phase is lower than body temperature during the high-temperature phase. To determine a date to be a reference during the low-temperature phase and a date to be a reference during the high-temperature phase, the regression equation obtainer 141 obtains the equation of the curve graph including a local minimum point and a local maximum point. The curve graph only needs to include a local minimum point and a local maximum point that can be identified, that is, the curve graph only needs to show a tendency of the low-temperature phase and the high-temperature phase that can be identified. Thus, a strict similarity between the graph of changes in body temperature data and the curve graph is not required. In FIG. 5A, the graph G4 is a curve graph that approximates the graph G3.

The reference body temperature determiner 142 determines a low-temperature-phase reference body temperature, based on a plurality of days of body temperatures that are identified based on the local minimum point on the curve graph. The reference body temperature determiner 142 also determines a high-temperature-phase reference body temperature, based on a plurality of days of body temperatures that are identified based on the local maximum point on the curve graph. The low-temperature-phase reference body temperature is a reference body temperature during the low-temperature phase. The high-temperature-phase reference body temperature is a reference body temperature during the high-temperature phase. The reference body temperature determiner 142 identifies the date corresponding to the local minimum point. Then, the reference body temperature determiner 142 may calculate the low-temperature-phase reference body temperature, for example, by averaging the body temperature data within a predetermined number of days before and after the identified date. The reference body temperature determiner 142 also identifies the date corresponding to the local maximum point. Then, the reference body temperature determiner 142 may calculate the high-temperature-phase reference body temperature, for example, by averaging the body temperature data within a predetermined number of days before and after the identified date.

Figure 5B:
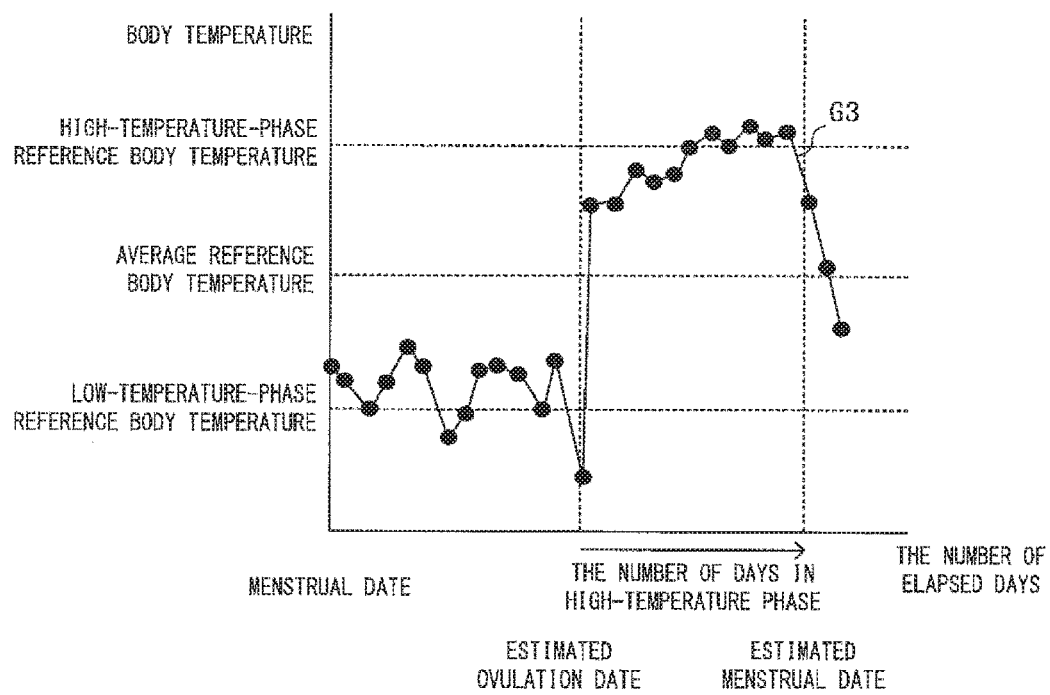
FIG. 5B is a diagram showing an example relationship between a graph G3 of changes in body temperature data and an estimated ovulation date.

The estimator 143 estimates an ovulation date, based on the determined low-temperature-phase reference body temperature and the determined high-temperature-phase reference body temperature. Specifically, the estimator 143 performs the estimation, based on a determination reference body temperature set at a value between the low-temperature-phase reference body temperature and the high-temperature-phase reference body temperature and on a plurality of days of body temperature data. For example, the estimator 143 may calculate the determination reference body temperature at the average value of the low-temperature-phase reference body temperature and the high-temperature-phase reference body temperature, and estimate the ovulation date, based on this average. This average value is referred to as an average reference body temperature. Alternatively, the estimator 143 may determine the determination reference body temperature, for example, to be within a body temperature range lower than the average value of the low-temperature-phase reference body temperature and the high-temperature-phase reference body temperature. FIG. 5B is a diagram showing an example relationship between the graph G3 of changes in body temperature data and the estimated ovulation date. For example, the estimator 143 may identify, as a reference date, the date on which the body temperature data changes from being lower than the average reference body temperature to being higher than the average reference body temperature. Thus, the timing of the transition from the low-temperature phase to the high-temperature phase can be caught. When the body temperature data on a certain date is higher than the average reference body temperature and the body temperature data on the day before the certain date is lower than the average reference body temperature, the certain date is the date on which the body temperature data becomes higher than the average reference body temperature. The day before the certain date may be, for example, one day before the certain date according to the calendar, or may be the date nearest to the certain date among the days on which body temperature data was successfully obtained before the certain date. When there are a plurality of days on which the body temperature data becomes higher than the average reference body temperature, the estimator 143 determines, for example, the earliest of the plurality of days to be the reference date. Then, the estimator 143 may estimate the day before the identified reference date to be the ovulation date. The ovulation date is not limited to the day before the reference date. For example, the estimator 143 may estimate the identified reference date to be the ovulation date. If the current time is within the low-temperature phase of the current menstrual cycle, the ovulation date is estimated to be a future date in the current menstrual cycle. If the current time is within the high-temperature phase of the current menstrual cycle, the ovulation date is estimated to be a past date in the current menstrual cycle.

The system controller 14 estimates an ovulation date, based on a low-temperature-phase reference body temperature and a high-temperature-phase reference body temperature that are determined by using the regression equation of a curve graph that approximates a graph of changes in body temperature. Thus, the effect of noise in actual measurements is reduced, and decrease in estimation accuracy is prevented even with less menstrual cycles of actual measurements. The system controller 14 corrects changes in body temperature during previous menstrual cycle(s) by using actual measurements during the current menstrual cycle to determine body temperature data, thus estimating an ovulation date based on changes in body temperature during the current menstrual cycle. In particular, the body temperature after entering the high-temperature phase in the current menstrual cycle is higher than that during the low-temperature phase. Thus, information about whether the timing of the transition to the high-temperature phase in the current menstrual cycle is earlier or later than that in the previous menstrual cycle(s) is reflected in the curve graph. Consequently, estimation accuracy is further improved.

The information processing server 1 may include a plurality of server devices. For example, a server device that obtains information from the user terminals 2, a server device that estimates an ovulation date and a menstrual date, a server device that provides information to the user terminals 2, a server device that manages databases, and other server devices may be connected to each other via a LAN or the like.

1-3. How Information Processing System Works

Figure 8:
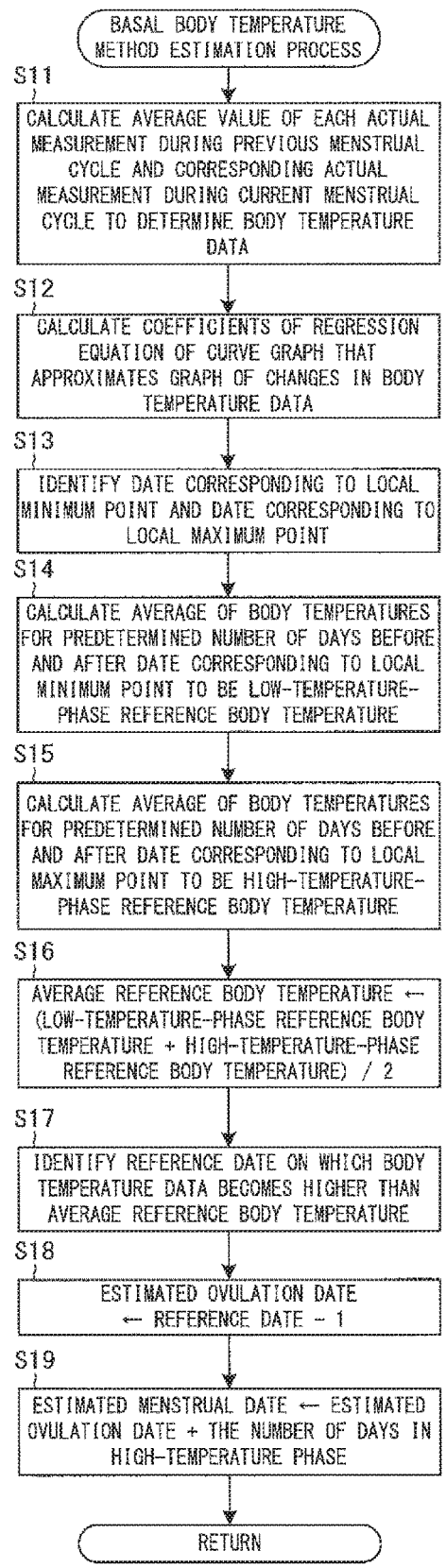
FIG. 8 is a flowchart showing an example process of a basal body temperature method estimation process in the system controller 14 of the information processing server 1 according to an embodiment.

The following describes how the information processing system S works, with reference to FIGS. 6 to 8.

FIG. 6 is a flowchart showing an example process of an estimation process in the system controller 14 of the information processing server 1 according to this embodiment. For example, in response to a user operation, the user terminal 2 sends an estimation request to the information processing server 1. The estimation request includes the user ID of a user who uses the user terminal 2. The system controller 14 may perform the estimation process when receiving the estimation request.

When the estimation process is started, the estimator 143 retrieves, from the body temperature DB 12b, all pairs of measurement dates and actual measurements that correspond to the user ID included in the estimation request, and stores them in the RAM 14c. The estimator 143 also retrieves, from the menstrual date DB 12c, menstrual dates that correspond to the user ID included in the estimation request, and stores them in the RAM 14c. The estimator 143 identifies the first day of each menstrual cycle, based on the retrieved menstrual dates. Then, as shown in FIG. 6, based on the measurement dates and the date of the first day of each menstrual cycle, the estimator 143 determines whether there are one or more menstrual cycles during which the user's body temperature was measured four or more times every week, among the three most recent previous menstrual cycles (Step S1). If the estimator 143 determines that there is no menstrual cycle during which the body temperature was measured four or more times every week (NO in Step S1), the process proceeds to Step S3. In Step S3, the estimator 143 sends a message indicating why it cannot perform the estimation to the user terminal 2. The user terminal 2 displays the received message on its screen. After Step S3, the estimator 143 terminates the estimation process. The number of the menstrual cycles may be other than three, and the number of times that the body temperature was measured may be other than four.

On the other hand, if the estimator 143 determines that there are one or more menstrual cycles during which the body temperature was measured four or more times every week (YES in Step S1), the process proceeds to Step S2. In Step S2, the estimator 143 determines whether the body temperature was measured four or more times every week during the current menstrual cycle (Step S2). If the estimator 143 determines that the body temperature was not measured four or more times every week (NO in Step S2), the process proceeds to Step S3. The number of times that the body temperature was measured may be other than four.

On the other hand, if the estimator 143 determines that the body temperature was measured four or more times every week (YES in Step S2), the process proceeds to Step S4. In Step S4, the estimator 143 performs a basal body temperature method estimation process. The basal body temperature method estimation process determines an estimated ovulation date and an estimated menstrual date by a basal body temperature method. The basal body temperature method estimation process is described in detail later. Subsequently, the estimator 143 sends the determined estimated ovulation date and the determined estimated menstrual date to the user terminal 2 (Step S5). The user terminal 2 displays the received estimated ovulation date and the received estimated menstrual date on the screen. FIG. 7 is a diagram showing an example screen display of an estimation result. As shown in FIG. 7, an estimated ovulation date D1, an estimated menstrual date D2, and other information are displayed. After Step S5, the estimator 143 terminates the estimation process.

FIG. 8 is a flowchart showing an example process of the basal body temperature method estimation process in the system controller 14 of the information processing server 1 according to this embodiment. When the basal body temperature method estimation process is started, the regression equation obtainer 141 selects one or more of the menstrual cycles during which the body temperature was measured four or more times every week, from among the three most recent previous menstrual cycles, as menstrual cycle(s) for determining body temperature data. For example, the regression equation obtainer 141 may select the latest menstrual cycle. Alternatively, the regression equation obtainer 141 may select the menstrual cycle including the largest number of dates on which the body temperature was measured. Alternatively, the regression equation obtainer 141 may obtain the regression equation of a curve graph that approximates a graph of changes in actual measurement, for each previous menstrual cycle. In this case, the reference body temperature determiner 142 may determine a low-temperature-phase reference body temperature and a high-temperature-phase reference body temperature during each menstrual cycle, and the estimator 143 may estimate an ovulation date and a menstrual date in each menstrual cycle. Then, the regression equation obtainer 141 may select the menstrual cycle including the estimated menstrual date that is nearest to the actual menstrual date. This improves estimation accuracy. Alternatively, the regression equation obtainer 141 may select a plurality of menstrual cycles.

After selecting a menstrual cycle, as shown in FIG. 8, the regression equation obtainer 141 determines body temperature data, based on actual measurements during the selected previous menstrual cycle and actual measurements during the current menstrual cycle (Step S11). Specifically, the regression equation obtainer 141 subtracts the first day of each menstrual cycle from each measurement date in the menstrual cycle to calculate the number of days that have elapsed since the first day. Subsequently, the regression equation obtainer 141 calculates the average of each pair of actual measurements whose numbers of the elapsed days are the same, between the previous and current menstrual cycles, to be body temperature data. If an actual measurement during one of the previous and current menstrual cycles was not obtained certain days after the corresponding first day, the regression equation obtainer 141 determines an actual measurement during the other menstrual cycle to be body temperature data. The regression equation obtainer 141 associates the body temperature data and the number of elapsed days with each other, and stores them as measurement data in the RAM 14c.

When a plurality of previous menstrual cycles of actual measurements are used, the regression equation obtainer 141 may calculate, for example, the average value of actual measurements among the plurality of previous menstrual cycles. Then, the regression equation obtainer 141 may calculate the average value of the calculated average value and an actual measurement during the current menstrual cycle to be body temperature data. The plurality of previous menstrual cycles may have different days. In this case, the regression equation obtainer 141 may simply calculate the average of each pair of actual measurements whose numbers of the elapsed days are the same. Alternatively, the regression equation obtainer 141 may subtract each measurement date in each menstrual cycle from the last day of the menstrual cycle to calculate the number of days until the last day. Then, the regression equation obtainer 141 may calculate the average of each pair of actual measurements whose numbers of days until the corresponding last day are the same. There is a small variation in the number of days between high-temperature phases as compared with a variation in the number of days between low-temperature phases. Thus, the regression equation obtainer 141 improves estimation accuracy by coordinating the high-temperature phases with each other between the menstrual cycles. In this case, for example, for the period between thirteen days before the last day of a menstrual cycle (fourteen days before the first day of the next menstrual cycle) and the last day of the menstrual cycle, the regression equation obtainer 141 may calculate the average of each pair of actual measurements whose numbers of days until the corresponding last day are the same. For the periods of fourteen days or more until the corresponding last day, the regression equation obtainer 141 may adjust the periods to each other between the plurality of menstrual cycles. For example, assume that there are a menstrual cycle A of twenty days and a menstrual cycle B of thirty days. In this case, for the last fourteen days of each menstrual cycle, the regression equation obtainer 141 calculates the average of each pair of actual measurements whose numbers of days until the corresponding last day are the same. Then, six days remain in the menstrual cycle A, and sixteen days remain in the menstrual cycle B. In this case, the regression equation obtainer 141 multiplies the number of days between the first day and each day of the first six days of the menstrual cycle A by sixteen sixths, and rounds off the calculations. Then, the regression equation obtainer 141 calculates the average of each pair of actual measurements whose numbers of days are the same, between the calculated number of days for the menstrual cycle A and the number of days since the first day of the menstrual cycle B.

There may be a case where the number of days in the current menstrual cycle has already exceeded the number of days in a previous menstrual cycle. In this case, the regression equation obtainer 141 may calculate the average of each pair of actual measurements whose numbers of days since the first day of the corresponding menstrual cycle are the same, for example, within the number of days in the previous menstrual cycle. Then, the regression equation obtainer 141 may determine body temperature data corresponding to the number of days in the previous menstrual cycle. Thus, the regression equation obtainer 141 obtains the average of changes in body temperature during the short low-temperature phase and changes in body temperature during the long low-temperature phase.

After Step S11, the regression equation obtainer 141 calculates each coefficient of the regression equation of a curve graph that approximates a graph of changes in the body temperature data, using regression analysis (Step S12). For example, the regression equation obtainer 141 may use the least-squares method. In this embodiment, the degree of the regression equation is predetermined.

Subsequently, based on each of the calculated coefficients, the reference body temperature determiner 142 identifies a local minimum point and a local maximum point on the curve graph defined by the regression equation, and identifies the date corresponding to the local minimum point and the date corresponding to the local maximum point in the form of the number of days since the first day of the menstrual cycle (Step S13). At this time, there may be a case where two or more local minimum points and two or more local maximum points appear. In this case, the reference body temperature determiner 142 may identify, for example, the maximum of the plurality of local maximum points. Then, the reference body temperature determiner 142 may identify, for example, the local minimum point that appears before and nearest to the date corresponding to the identified local maximum point, from among the plurality of local minimum points.

Next, the reference body temperature determiner 142 calculates the average of the body temperature data for a predetermined number of days before and after the date corresponding to the local minimum point to be a low-temperature-phase reference body temperature (Step S14). Then, the reference body temperature determiner 142 calculates the average of the body temperature data for the predetermined number of days before and after the date corresponding to the local maximum point to be a high-temperature-phase reference body temperature (Step S15). The predetermined number of days may be, for example, three days.

After that, the estimator 143 calculates the average value of the low-temperature-phase reference body temperature and the high-temperature-phase reference body temperature to be an average reference body temperature (Step S16). Subsequently, the estimator 143 identifies a reference date on which the body temperature data becomes higher than the average reference body temperature (Step S17). For example, for each day from the first day to the last day of the menstrual cycle, the estimator 143 determines whether the body temperature data is higher than the average reference body temperature. Then, the estimator 143 calculates the reference date on which the body temperature data becomes higher than the average reference body temperature, by adding the number of the elapsed days corresponding to the date on which the body temperature data is first determined to be higher than the average reference body temperature to the date of the first day of the current menstrual cycle.

Subsequently, the estimator 143 subtracts 1 from the identified reference date to calculate an estimated ovulation date (Step S18). Based on the estimated ovulation date, the estimator 143 estimates a menstrual date (Step S19). For example, the estimator 143 may add the number of days in the high-temperature phase to the estimated ovulation date to calculate the estimated menstrual date. In this case, the estimator 143 may estimate the menstrual date, for example, by the rhythm method. Specifically, the estimator 143 adds fourteen days to the estimated ovulation date to calculate the estimated menstrual date. Alternatively, the estimator 143 may estimate an ovulation date in each previous menstrual cycle, for example, by the above-described method, and calculate the number of days from the ovulation date to the actual menstrual date to be the number of days in the high-temperature phase of the menstrual cycle. Then, the estimator 143 may calculate the average value of the calculated numbers of days and then add the average value to the estimated ovulation date, to calculate the estimated menstrual date. After Step S19, the estimator 143 terminates the basal body temperature method estimation process.

As described above, according to this embodiment, the system controller 14 obtains the regression equation of a function of date that approximates the relationship between body temperature data, which is obtained based on actual measurements during at least one menstrual cycle, and dates, and that has a local minimum value and a local maximum value. The system controller 14 also determines a low-temperature-phase reference body temperature, based on a plurality of days of body temperatures that are identified based on the date corresponding to a local minimum value in the function defined by the regression equation, and determines a high-temperature-phase reference body temperature, based on a plurality of days of body temperatures that are identified based on the date corresponding to a local maximum value in the function. Then, the system controller 14 estimates an ovulation date in the current menstrual cycle, based on a determination reference body temperature set at a value between the low-temperature-phase reference body temperature and the high-temperature-phase reference body temperature and on measurement data. Thus, it becomes possible to estimate an ovulation date using less menstrual cycles of body temperatures while preventing decrease in estimation accuracy.

Typically, one menstrual cycle includes a low-temperature phase and a high-temperature phase, and an ovulation date comes at the transition from the low-temperature phase to the high-temperature phase. However, it is difficult for a computer to determine which body temperature was measured during the low-temperature phase and which body temperature was measured during the high-temperature phase from changes in actual measurement of body temperature. Thus, it has been difficult to estimate an ovulation date. According to this embodiment, to identify which date is included in the low-temperature phase and which date is included in the high-temperature phase, the system controller 14 derives a function having a local minimum value and a local maximum value from measurement data (a graph of changes in body temperature data). Thus, an ovulation date is estimated from less menstrual cycles body temperatures.

The system controller 14 may identify a date on which body temperature becomes higher than the determination reference body temperature, among the dates included in the measurement data, as a reference date, and estimate an ovulation date, based on the reference date. This allows an ovulation date to be correctly estimated.

The system controller 14 may obtain the regression equation of a function that approximates the relationship between body temperature data and dates, which is obtained based on actual measurements during at least one previous menstrual cycle and on actual measurements during the current menstrual cycle. This allows changes in actual measurement during the current menstrual cycle to be reflected in the function. Consequently, estimation accuracy is improved.

2. Second Embodiment

Figure 9:
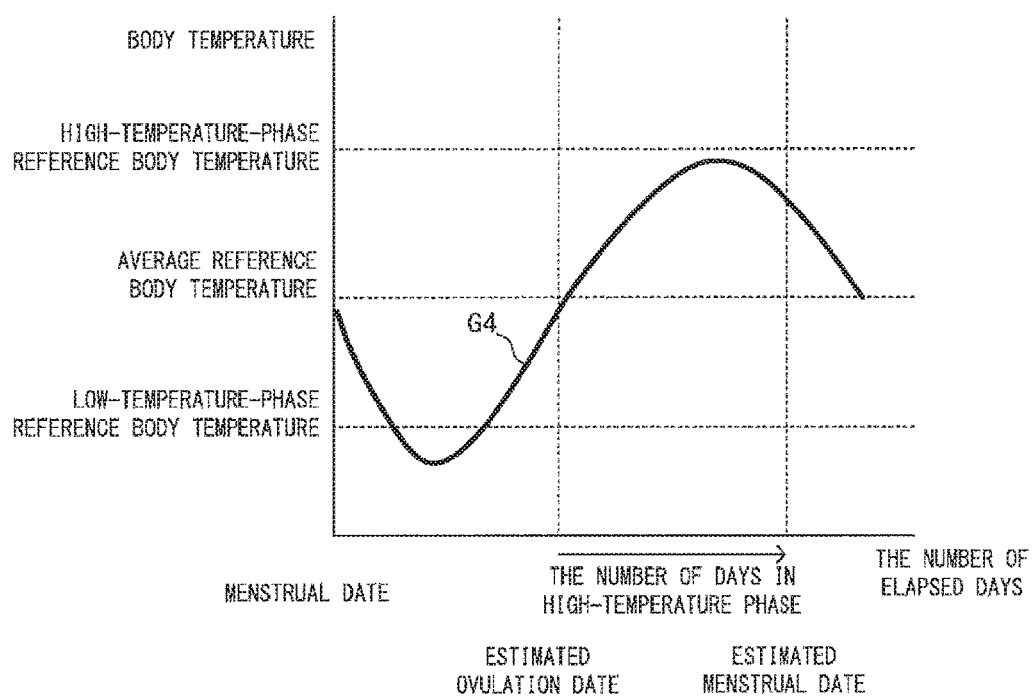
FIG. 9 is a diagram showing an example relationship between a curve graph G4 and an estimated ovulation date.
Figure 10:
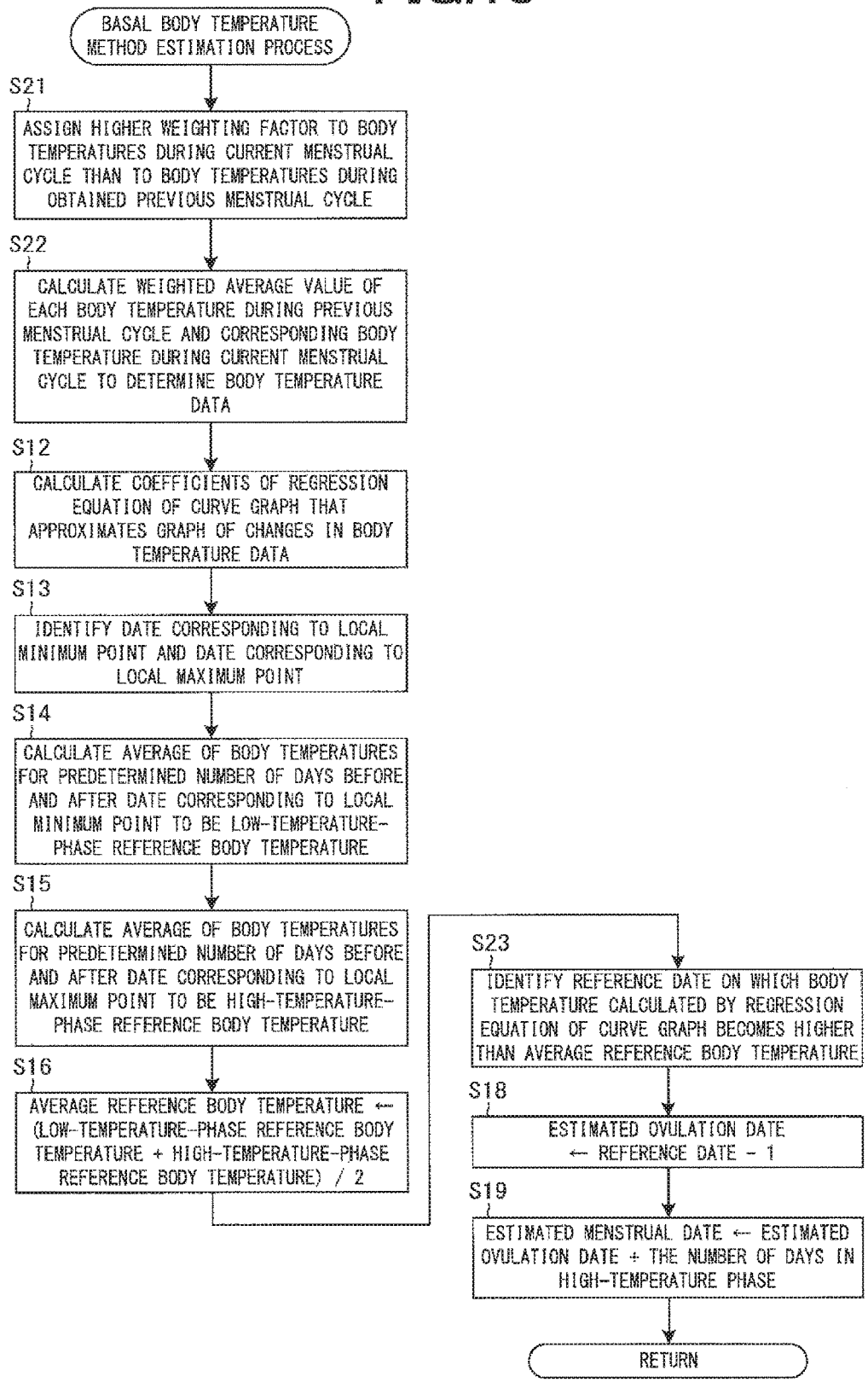
FIG. 10 is a flowchart showing an example process of the basal body temperature method estimation process in the system controller 14 of the information processing server 1 according to an embodiment.

The following describes a second embodiment with reference to FIGS. 9 and 10. The configuration of the information processing system S, the configuration of the information processing server 1, and the functional blocks of the system controller 14 are the same as those in the first embodiment.

In the first embodiment, after a low-temperature-phase reference body temperature and a high-temperature-phase reference body temperature are determined, the system controller 14 estimates an ovulation date using a graph of changes in body temperature data. In this embodiment, the system controller 14 estimates an ovulation date by using the regression equation of a curve graph. FIG. 9 is a diagram showing an example relationship between the curve graph G4 and an estimated ovulation date. For example, as shown in FIG. 9, the estimator 143 may identify on which date the body temperature calculated by the regression equation of the curve graph becomes higher than the average value of a low-temperature-phase reference body temperature and a high-temperature-phase reference body temperature. Then, the estimator 143 may estimate the day before the identified date to be the ovulation date.

When determining body temperature data, the system controller 14 may calculate a weighted average of each actual measurement during a previous menstrual cycle and the corresponding actual measurement during the current menstrual cycle. In this case, the system controller 14 sets the weighting factor of the actual measurements during the current menstrual cycle to a value higher than the weighting factor of the actual measurements during the previous menstrual cycle. The length of the low-temperature phase of the current menstrual cycle has great effect on the next menstrual date and the ovulation date in the current menstrual cycle, as compared with the low-temperature phase of the previous menstrual cycle. Assigning a higher weight to the actual measurements during the current menstrual cycle improves estimation accuracy. For example, each weighting factor may be prestored in the storage unit 12. For example, the weighting factor of the actual measurements during the current menstrual may be 0.7 and the weighting factor of the actual measurements during the previous menstrual cycle may be 0.3.

FIG. 10 is a flowchart showing an example process of the basal body temperature method estimation process in the system controller 14 of the information processing server 1 according to this embodiment. In FIG. 10, the same steps as in FIG. 8 are denoted by the same reference signs. As shown in FIG. 10, the regression equation obtainer 141 assigns a higher weighting factor to actual measurements during the current menstrual cycle than to actual measurements during a previous menstrual cycle (Step S21). For example, the regression equation obtainer 141 retrieves each preset weighting factor from the storage unit 12. Then, based on the retrieved weighting factors, the regression equation obtainer 141 calculates a weighted average of each actual measurement during the previous menstrual cycle and the corresponding actual measurement during the current menstrual cycle, and determines the weighted averages to be body temperature data (Step S22). Except for calculating the weighted averages, the details of Step S22 are the same as those of Step S11 shown in FIG. 8. Subsequently, Steps S12 to S16 are performed.

After that, the estimator 143 identifies a reference date on which the body temperature calculated by the regression equation becomes higher than the average reference body temperature (Step S23). Specifically, for each day from the first day to the last day of the menstrual cycle, the estimator 143 calculates a body temperature given by the regression equation, based on each coefficient determined in Step S12. Next, for each day from the first day to the last day of the menstrual cycle, the estimator 143 determines whether the calculated body temperature is higher than the average reference body temperature. Then, the estimator 143 calculates the reference date by adding the number of the elapsed days corresponding to the date on which the calculated body temperature is first determined to be higher than the average reference body temperature to the date of the first day of the current menstrual cycle. Subsequently, Steps S18 and S19 are performed.

As described above, according to this embodiment, the system controller 14 estimates an ovulation date, based on the date on which the body temperature calculated by using the regression equation becomes higher than the determination reference body temperature. Consequently, decrease in estimation accuracy due to the effect of noise in actual measurements is prevented.

The system controller 14 may assign a higher weight to actual measurements during the current menstrual cycle than to actual measurements during a previous menstrual cycle, calculate a weighted average of each actual measurement during the previous menstrual cycle and the corresponding actual measurement during the current menstrual cycle, and obtain the regression equation of a function that approximates the relationship between body temperature data including the weighted averages and dates. This allows changes in body temperature during the current menstrual cycle to be further reflected in the function. Consequently, estimation accuracy is improved.

3. Third Embodiment

The following describes a third embodiment with reference to FIGS. 11 to 13B. The configuration of the information processing system S and the configuration of the information processing server 1 are the same as those in the first embodiment.

In this embodiment, when obtaining the regression equation of a curve graph, the system controller 14 selects the degree of a regression equation used to estimate an ovulation date, from among a plurality of degrees. Specifically, the system controller 14 estimates a menstrual date in a previous menstrual cycle by using each of the regression equations of the plurality of degrees. Then, the system controller 14 selects the degree that minimizes the difference between the estimated menstrual date and the actual menstrual date. That is, the system controller 14 uses the degree that maximizes estimation accuracy of a previous menstrual date.

3-1. Functional Configuration of System Controller

Figure 11:
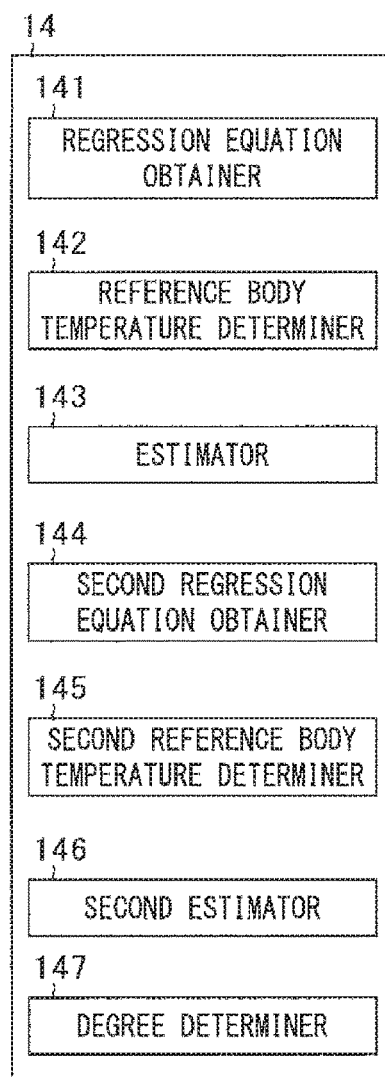
FIG. 11 is a diagram showing example functional blocks of the system controller 14 according to an embodiment.

FIG. 11 is a diagram showing example functional blocks of the system controller 14 according to this embodiment. In FIG. 11, the same components as in FIG. 2B are denoted by the same reference signs. As shown in FIG. 11, the system controller 14 functions as, for example, the regression equation obtainer 141, the reference body temperature determiner 142, the estimator 143, a second regression equation obtainer 144, a second reference body temperature determiner 145, a second estimator 146, and a degree determiner 147. The second regression equation obtainer 144 is an example of second obtaining means of the present invention. The second reference body temperature determiner 145 is an example of second determining means of the present invention. The second estimator 146 is an example of second estimating means of the present invention. The degree determiner 147 is an example of identifying means of the present invention.

The second regression equation obtainer 144 obtains curve graph regression equations that each approximate a graph of changes in actual measurement during at least one previous menstrual cycle. The second regression equation obtainer 144 differs from the regression equation obtainer 141 in that it uses actual measurements during the previous menstrual cycle(s) and no body temperature data, that is, in that it uses no actual measurements during the current menstrual cycle. In the other respects, the second regression equation obtainer 144 is the same as the regression equation obtainer 141. For example, the regression equation obtainer 141 may double as the second regression equation obtainer 144.

For each of the regression equations obtained by the second regression equation obtainer 144, the second reference body temperature determiner 145 determines a low-temperature-phase reference body temperature and a high-temperature-phase reference body temperature during a previous menstrual cycle, based on the regression equation. The second reference body temperature determiner 145 determines them in the same manner as the reference body temperature determiner 142. For example, the reference body temperature determiner 142 may double as the second reference body temperature determiner 145.

For each of the regression equations obtained by the second regression equation obtainer 144, the second estimator 146 estimates an ovulation date and a menstrual date, based on the low-temperature-phase reference body temperature and the high-temperature-phase reference body temperature that are determined by the second reference body temperature determiner 145. The second estimator 146 estimates them in the same manner as the estimator 143. For example, the estimator 143 may double as the second estimator 146.

The degree determiner 147 identifies the regression equation that minimizes the difference between the menstrual date estimated by the second estimator 146 and a previous actual menstrual date, from among the regression equations obtained by the second regression equation obtainer 144. Then, the degree determiner 147 selects the degree of the identified regression equation as the degree for estimating an ovulation date in the current menstrual cycle.

3-2. How Information Processing System Works

Figure 12:
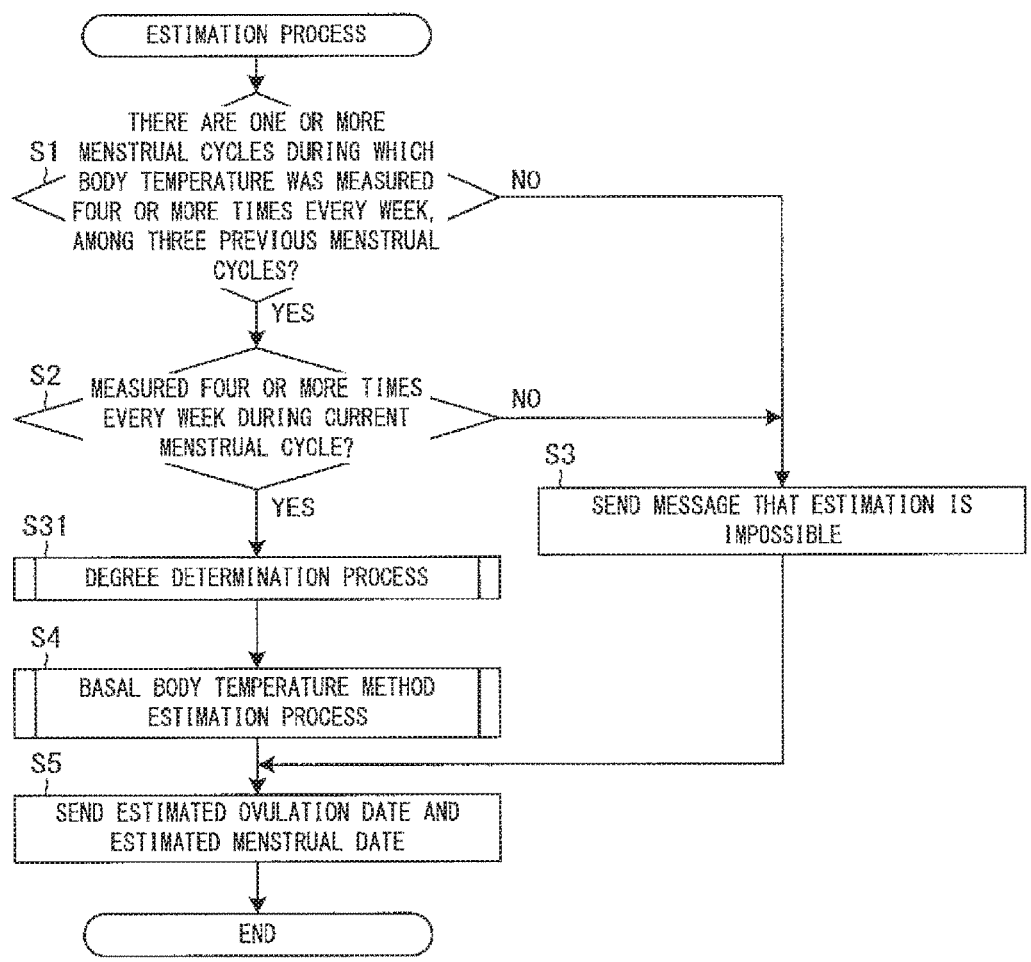
FIG. 12 is a flowchart showing an example process of the estimation process in the system controller 14 of the information processing server 1 according to an embodiment.
Figure 13A:
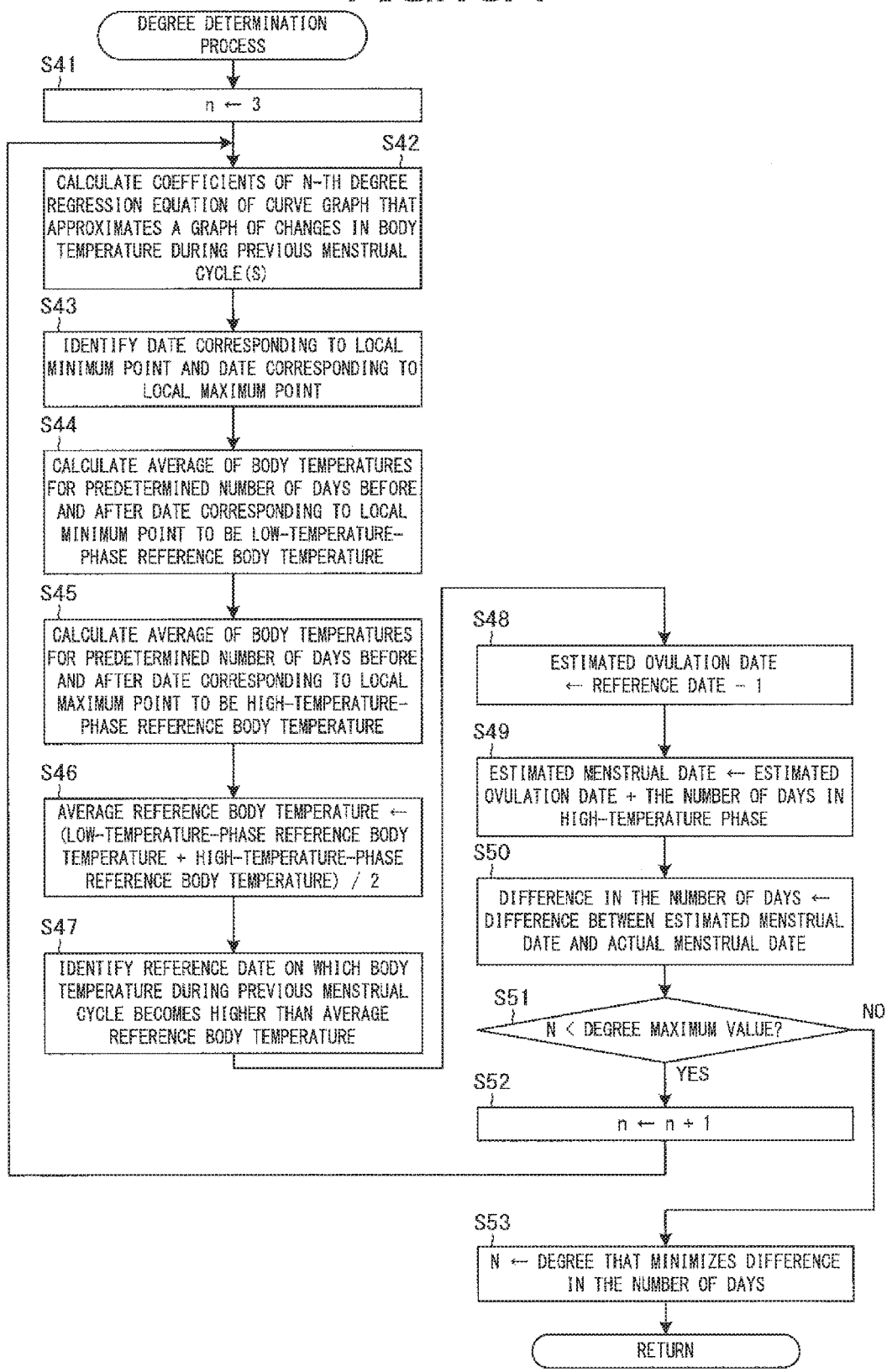
FIG. 13A is a flowchart showing an example process of a degree determination process in the system controller 14 of the information processing server 1 according to an embodiment.
Figure 13B:
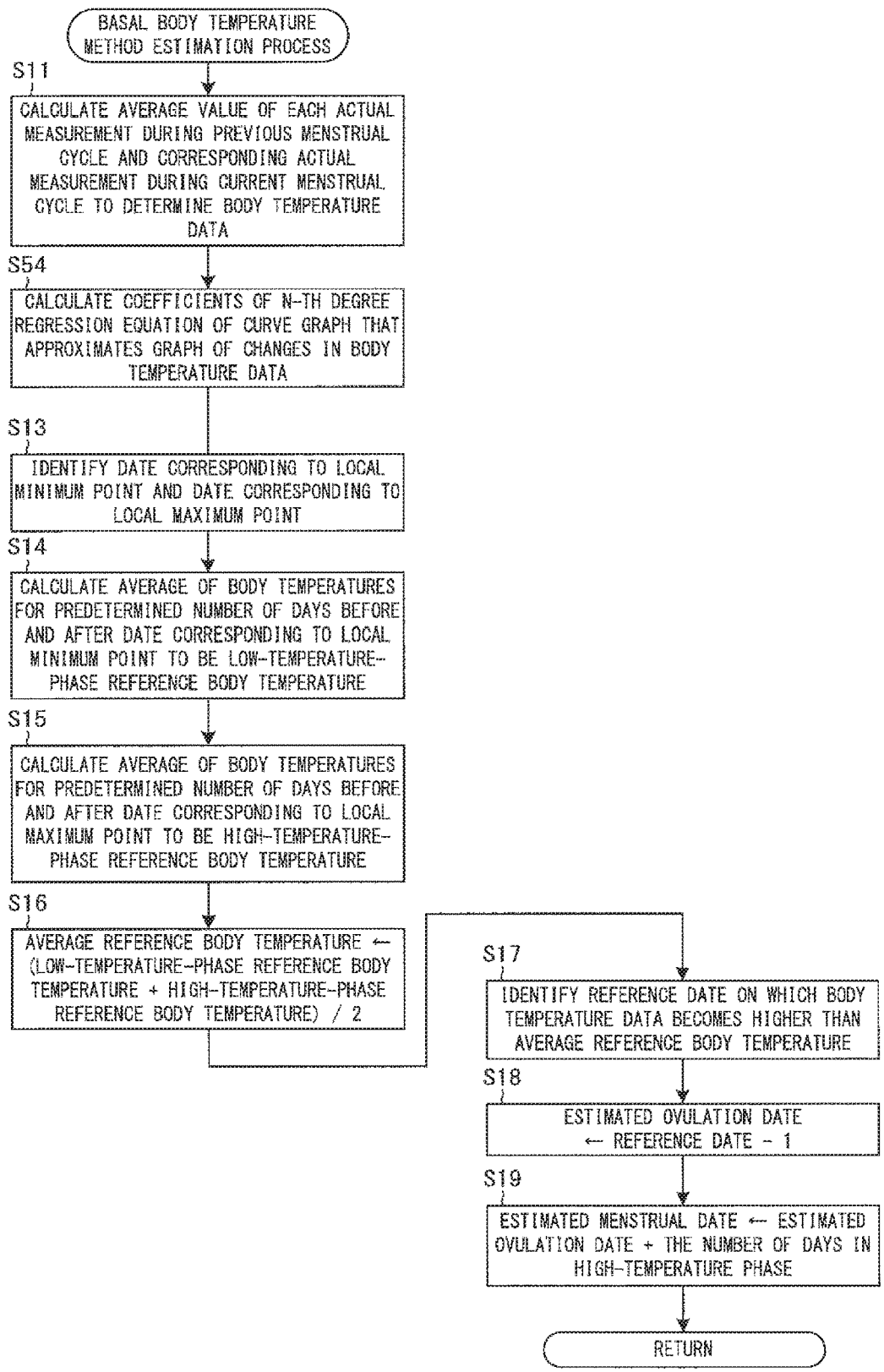
FIG. 13B is a flowchart showing an example process of the basal body temperature method estimation process in the system controller 14 of the information processing server 1 according to an embodiment.

The following describes how the information processing system S works, with reference to FIGS. 12, 13A, and 13B.

FIG. 12 is a flowchart showing an example process of the estimation process in the system controller 14 of the information processing server 1 according to this embodiment. In FIG. 12, the same steps as in FIG. 6 are denoted by the same reference signs. As shown in FIG. 12, if the estimator 143 determines in Step S2 that the body temperature was measured four or more times every week during the current menstrual cycle (YES in Step S2), the process proceeds to Step S31. In Step S31, the system controller 14 performs a degree determination process. The degree determination process determines the degree of a regression equation. The degree determination process is described in detail below. Subsequently, the estimator 143 performs Steps S4 and S5, and then terminates the estimation process.

FIG. 13A is a flowchart showing an example process of the degree determination process in the system controller 14 of the information processing server 1 according to this embodiment. When the degree determination process is started, the second regression equation obtainer 144 selects one or more of the menstrual cycles during which the body temperature was measured four or more times every week, from among the three most recent previous menstrual cycles. The menstrual cycles) are selected in the same manner as in the basal body temperature method estimation process. Subsequently, as shown in FIG. 13A, the degree determiner 147 set a degree n to 3 (Step S41). Then, the second regression equation obtainer 144 calculates each coefficient of the n-th degree regression equation of a curve graph that approximates a graph of changes in actual measurement during the selected menstrual cycle(s) (Step S42).

Subsequently, based on each of the calculated coefficients, the second reference body temperature determiner 145 identifies the date corresponding to a local minimum point on the curve graph defined by the n-th degree regression equation and the date corresponding to a local maximum point on the curve graph (Step S43). Next, the second reference body temperature determiner 145 calculates the average of the actual measurements for a predetermined number of days before and after the date corresponding to the local minimum point to be a low-temperature-phase reference body temperature (Step S44). Then, the second reference body temperature determiner 145 calculates the average of the actual measurements for a predetermined number of days before and after the date corresponding to the local maximum point to be a high-temperature-phase reference body temperature (Step S45).

After that, the second estimator 146 calculates the average value of the low-temperature-phase reference body temperature and the high-temperature-phase reference body temperature to be an average reference body temperature (Step S46). Then, the second estimator 146 identifies a date on which the actual measurement becomes higher than the average reference body temperature (Step S47). Subsequently, the second estimator 146 subtracts 1 from the identified date to calculate an estimated ovulation date (Step S48). Based on the estimated ovulation date, the second estimator 146 estimates a menstrual date (Step S49).

Next, the degree determiner 147 calculates the difference between the menstrual date estimated in Step S49 and an actual menstrual date in the selected menstrual cycle(s) to be the difference in the number of days that corresponds to the degree n (Step S50). Then, the degree determiner 147 determines whether the degree n is less than a predetermined degree maximum value (Step S51). If the degree determiner 147 determines that the degree n is less than the degree maximum value (YES in Step S51), the process proceeds to Step S52. In Step S52, the degree determiner 147 adds 1 to the degree n. After that, the estimator 147 causes the process to proceed to Step S42.

On the other hand, if the degree determiner 147 determines that the degree n is not less than the degree maximum value (NO in Step S51), the process proceeds to Step S53. In Step S53, the degree determiner 147 identifies which of the degrees from 3 to the degree maximum value minimizes the difference in the number of days. Then, the degree determiner 147 sets a determined degree N to the identified degree. After Step S53, the degree determiner 147 terminates the degree determination process.

FIG. 13B is a flowchart showing an example process of the basal body temperature method estimation process in the system controller 14 of the information processing server 1 according to this embodiment. In FIG. 13B, the same steps as in FIG. 8 are denoted by the same reference signs. As shown in FIG. 13B, after Step S11, the regression equation obtainer 141 calculates each coefficient of the N-th degree regression equation of a curve graph that approximates a graph of changes in the body temperature data (Step S54). Then, Steps S13 to S19 are performed.

As described above, according to this embodiment, the system controller 14 obtains a plurality of regression equations of mutually different degrees. For each of the regression equations, the system controller 14 determines a low-temperature-phase reference body temperature and a high-temperature-phase reference body temperature. For each of the regression equations, the system controller 14 also estimates a menstrual date in at least one previous menstrual cycle, based on a body temperature set at a value between the low-temperature-phase reference body temperature and the high-temperature-phase reference body temperature and on a plurality of days of actual measurements. The system controller 14 also identifies the degree of the regression equation that minimizes the difference between the estimated menstrual date and the actual menstrual date, from among the plurality of regression equations. Then, the system controller 14 obtains the regression equation of the identified degree for estimating an ovulation date in the current menstrual cycle. Consequently, estimation accuracy is improved.

4. Fourth Embodiment

The following describes a fourth embodiment with reference to FIGS. 14 to 16B. The configuration of the information processing system S and the configuration of the information processing server 1 are the same as those in the first embodiment.

In this embodiment, the system controller 14 determines the reliability of actual measurements during the current menstrual cycle. If the reliability is low, the system controller 14 does not use the actual measurements during the current menstrual cycle, to estimate an ovulation date. In this case, the system controller 14 estimates an ovulation date, based on actual measurements during previous menstrual cycle(s) For example, the system controller 14 may calculate the number of days in a previous menstrual cycle using menstrual dates in previous menstrual cycles, and perform the estimation based on the calculated number of days. Alternatively, the system controller 14 may obtain the regression equation of a curve graph by using the actual measurements during the previous menstrual cycle(s), and perform the estimation based on the regression equation.

4-1. Functional Configuration of System Controller

Figure 14:
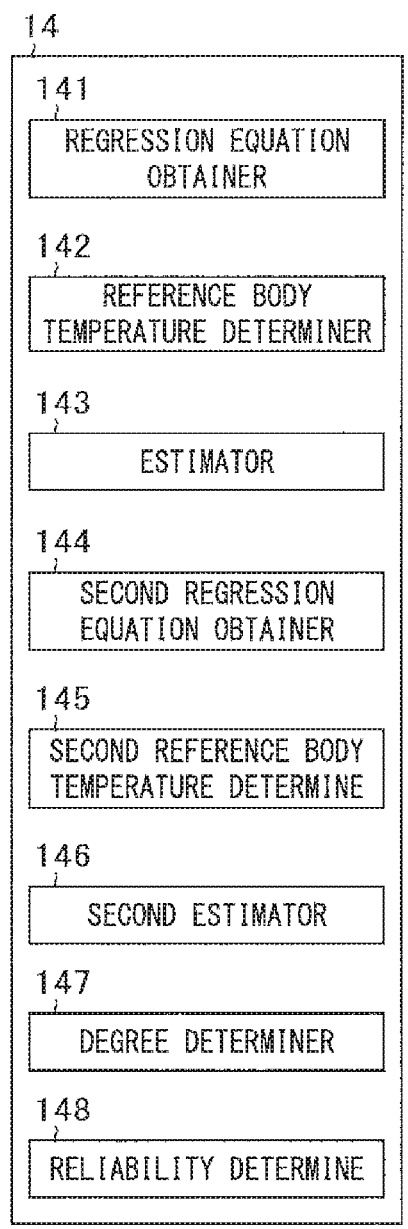
FIG. 14 is a diagram showing example functional blocks of the system controller 14 according to an embodiment.

FIG. 14 is a diagram showing example functional blocks of the system controller 14 according to this embodiment. In FIG. 14, the same components as in FIG. 11 are denoted by the same reference signs. As shown in FIG. 14, the system controller 14 functions as, for example, the regression equation obtainer 141, the reference body temperature determiner 142, the estimator 143, the second regression equation obtainer 144, the second reference body temperature determiner 145, the second estimator 146, the degree determiner 147, and a reliability determiner 148. The reliability determiner 148 is an example of determination means of the present invention.

The reliability determiner 148 determines the reliability of actual measurements during the current menstrual cycle, based on actual measurement during previous menstrual cycle(s). For example, the reliability determiner 148 may use the number of days in the low-temperature phase of a previous menstrual cycle that is identified based on an estimated ovulation date in the previous menstrual cycle, a low-temperature-phase reference body temperature, and a low-temperature-phase reference body temperature. Specifically, if the actual measurements during the low-temperature phase of the current menstrual cycle exceed the average value of the low-temperature-phase reference body temperature and the high-temperature-phase reference body temperature for at least a predetermined number of consecutive days, the reliability determiner 148 may determine that they are unreliable. In this case, for example, the user's physical condition may have changed during the current menstrual cycle.

4-2. How Information Processing System Works

Figure 15:
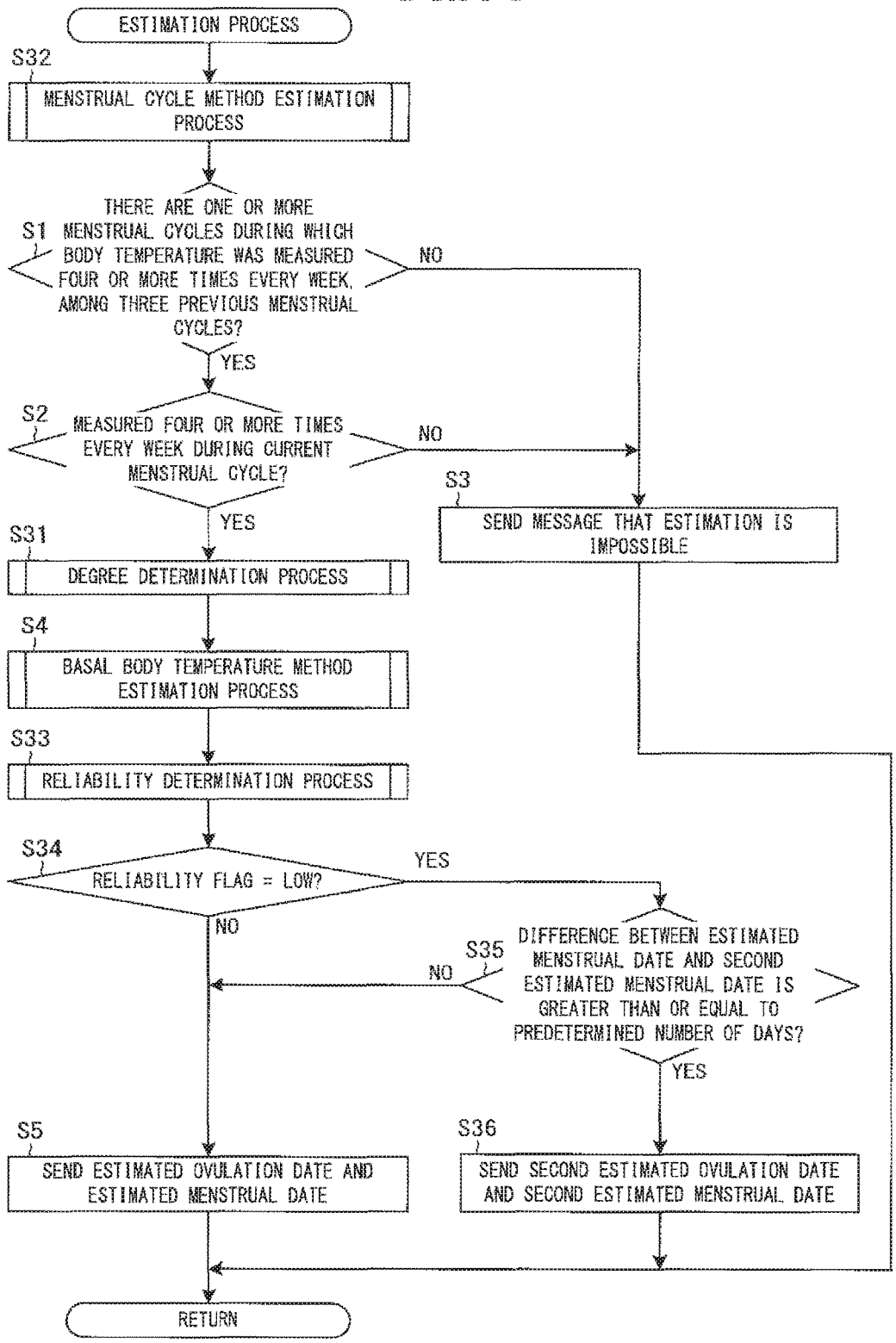
FIG. 15 is a flowchart showing an example process of the estimation process in the system controller 14 of the information processing server 1 according to an embodiment.
Figure 16A:
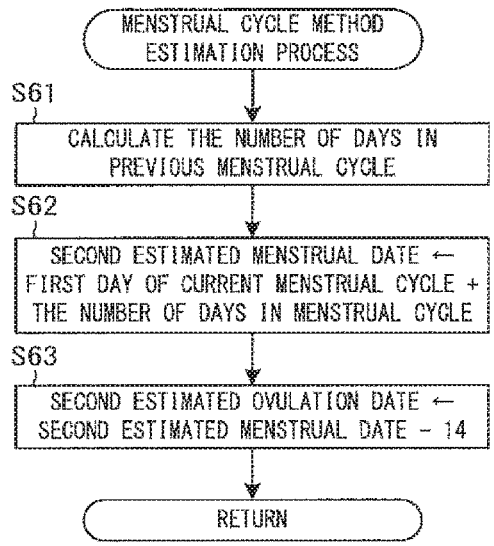
FIG. 16A is a flowchart showing an example process of a menstrual cycle method estimation process in the system controller 14 of the information processing server 1 according to an embodiment.
Figure 16B:
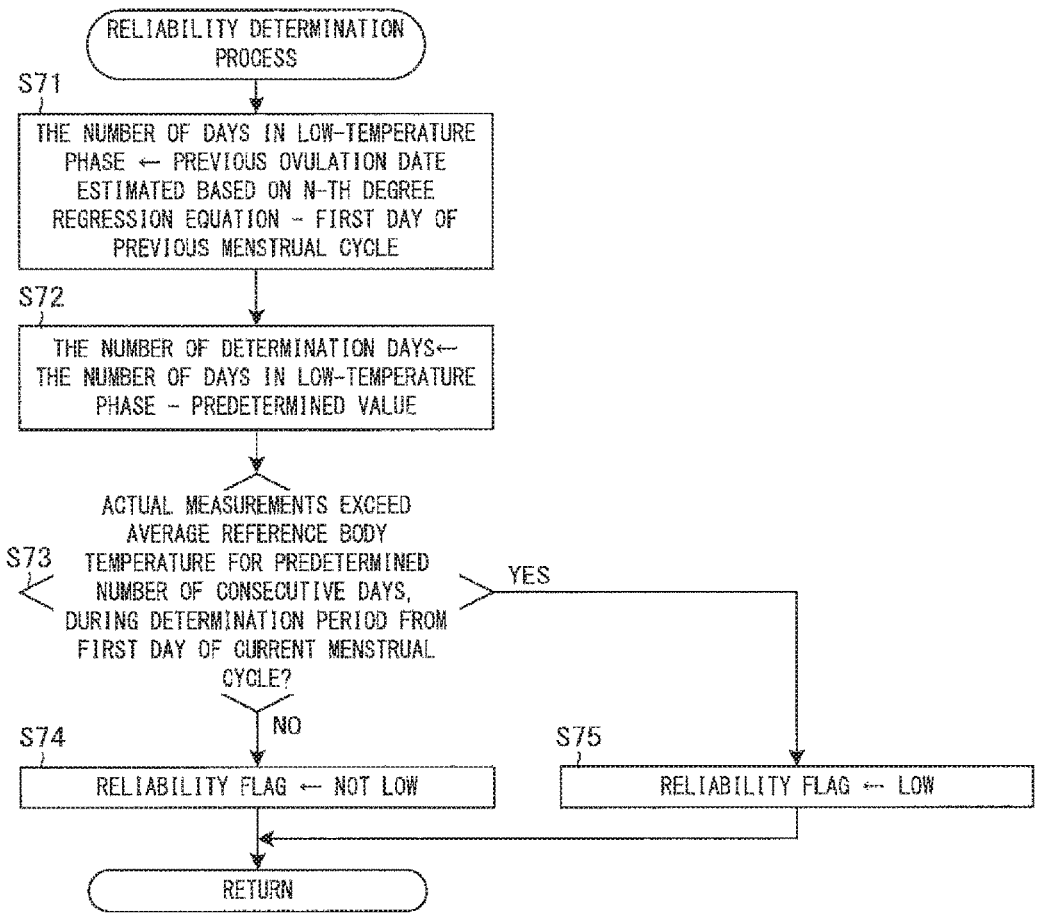
FIG. 16B is a flowchart showing an example process of a reliability determination process in the system controller 14 of the information processing server 1 according to an embodiment.

The following describes how the information processing system S works, with reference to FIGS. 15, 16A, and 16B.

FIG. 15 is a flowchart showing an example process of the estimation process in the system controller 14 of the information processing server 1 according to this embodiment. In FIG. 15, the same steps as in FIG. 12 are denoted by the same reference signs. As shown in FIG. 15, the estimator 143 performs a menstrual cycle method estimation process (Step S32). The menstrual cycle method estimation process estimates an ovulation date and a menstrual date, based on previous menstrual cycle(s). The ovulation date and the menstrual date that are estimated in the menstrual cycle method estimation process are respectively referred to as a second estimated ovulation date and a second estimated menstrual date. Subsequently, Steps S1 and S2 are performed. In Step S3, if the estimator 143 determines that the body temperature was measured four or more times every week (YES in Step S2), the process proceeds to Step S31. In Step, the estimator 143 performs the basal body temperature method estimation process, and then the estimator 143 performs the basal body temperature method estimation process (Step S4).

Next, the reliability determiner 148 performs a reliability determination process (Step S33). The reliability determination process determines the reliability of actual measurements during the current menstrual cycle. Then, a reliability flag is set based on the determination result. The reliability determination process is described in detail later. After that, the estimator 143 determines whether the reliability flag is set to "low" (Step S34). If the estimator 143 determines that the reliability flag is not set to "low" (NO in Step S34), the process proceeds to Step S5.

On the other hand, if the estimator 143 determines that the reliability flag is set to "low" (YES in Step S34), the process proceeds to Step S35. In Step S35, the reliability determiner 148 determines whether the difference between the menstrual date estimated in the basal body temperature method estimation process and the second estimated menstrual date estimated in the menstrual cycle method estimation process is greater than or equal to a predetermined number of days. If the reliability determiner 148 determines that the difference is not greater than or equal to the predetermined number of days (NO in Step S35), the process proceeds to Step S5. On the other hand, if the reliability determiner 148 determines that the difference is greater than or equal to the predetermined number of days (YES in Step S35), the process proceeds to Step S36. In Step S36, the estimator 143 sends the second estimated ovulation date and the second estimated menstrual date to the user terminal 2. The user terminal 2 displays the second estimated ovulation date and the second estimated menstrual, which are received from the information processing server 1, on the screen. Alternatively, the estimator 143 may send the ovulation date and the menstrual date that are estimated based on the N-th degree regression equation obtained in the degree determination process. The degree determination process uses no actual measurements during the current menstrual cycle, to estimate the ovulation date and the menstrual date. After Step S36, the estimator 143 terminates the estimation process.

When the reliability flag is set to "low", the reliability determiner 148 may skip the determination of Step S35, and the estimator 143 may send the second estimated ovulation date and the second estimated menstrual date.

FIG. 16A is a flowchart showing an example process of the menstrual cycle method estimation process in the system controller 14 of the information processing server 1 according to this embodiment. As shown in FIG. 16A, the estimator 143 calculates the number of days in a previous menstrual cycle, based on menstrual dates retrieved from the menstrual date DB 12c (Step S61). At this time, the estimator 143 may calculate, for example, the number of days in the latest menstrual cycle. Alternatively, the estimator 143 may calculate, for example, the average value of the numbers of days in a plurality of menstrual cycles. Subsequently, the estimator 143 adds the calculated number of days in the menstrual cycle to the date of the first day of the current menstrual cycle to calculate a second estimated menstrual date (Step S62). Then, the estimator 143 subtracts fourteen days from the second estimated menstrual date to calculate a second estimated ovulation date (Step S63). After Step S63, the estimator 143 terminates the menstrual cycle method estimation process.

FIG. 16B is a flowchart showing an example process of the reliability determination process in the system controller 14 of the information processing server 1 according to this embodiment. As shown in FIG. 16B, the reliability determiner 148 obtains the ovulation date in the previous menstrual cycle that is estimated based on the N-th degree regression equation obtained in the degree determination process. Then, the reliability determiner 148 subtracts the date of the first day of the menstrual cycle from the obtained ovulation date to calculate the number of days in the low-temperature phase (Step S71). Subsequently, the reliability determiner 148 subtracts a preset number of days from the number of days in the low-temperature phase to calculate the number of days in a determination period (Step S72). Next, the reliability determiner 148 obtains the average reference body temperature determined based on the N-th degree regression equation obtained in the degree determination process. After that, the reliability determiner 148 obtains actual measurements for the number of days corresponding to the number of days in the determination period from the first day of the current menstrual cycle. Then, the reliability determiner 148 determines whether the actual measurements exceed the average reference body temperature for a predetermined number of consecutive days during the determination period from the first day of the current menstrual cycle (Step S73).

If the reliability determiner 148 determines that the actual measurements do not exceed the average reference body temperature for the predetermined number of consecutive days (NO in Step S73), the process proceeds to Step S74. In Step S74, the reliability determiner 148 sets the reliability flag to "not low". On the other hand, if the reliability determiner 148 determines that the actual measurements exceed the average reference body temperature for the predetermined number of consecutive days (YES in Step S73), the process proceeds to Step S75. In Step S75, the reliability determiner 148 sets the reliability flag to "low". After Step S73 or S74, the reliability determiner 148 terminates the reliability determination process.

As described above, according to this embodiment, the system controller 14 determines whether the reliability of actual measurements during the current menstrual cycle meets a predetermined requirement, based on actual measurements during at least one previous menstrual cycle. If the reliability does not meet the predetermined requirement, the system controller 14 obtains a regression equation based on information about the at least one previous menstrual cycle, without using either a low-temperature-phase reference body temperature or a high-temperature-phase reference body temperature that is determined based on the actual measurements during the current menstrual cycle. Consequently, decrease in estimation accuracy due to using actual measurements during the current menstrual cycle is prevented.

The degree of the regression equation of the curve graph may be preset. In this case, the system controller 14 may skip the degree determination process. The basal body temperature method estimation process may be the same as that in the first or second embodiment. The system controller 14 may obtain a regression equation of the preset degree as the regression equation of a curve graph that approximates a graph of changes in actual measurement during the previous menstrual cycle(s), and calculate, for example, the number of days in the low-temperature phase, a low-temperature-phase reference body temperature, and a high-temperature-phase reference body temperature. Then, the system controller 14 may perform the reliability determination process, based on the calculated information.

5. Fifth Embodiment

The following describes a fifth embodiment with reference to FIG. 17. The configuration of the information processing system S, the configuration of the information processing server 1, and the functional blocks of the system controller 14 are the same as those in the fourth embodiment. Also in this embodiment, the system controller 14 determines the reliability of actual measurements during the current menstrual cycle. For example, if no actual measurement has yet exceeded the average of the low-temperature-phase reference body temperature and the high-temperature-phase reference body temperature even a predetermined number of days before the menstrual date estimated in the menstrual cycle method estimation process, the reliability determiner 148 may determine that the reliability is low. In this case, the current menstrual cycle is likely to end before a high-temperature phase appears.

FIG. 17 is a flowchart showing an example process of the reliability determination process in the system controller 14 of the information processing server 1 according to this embodiment. The estimation process, the menstrual cycle method estimation process, and the basal body temperature method estimation process are the same as those in the fourth embodiment. As shown in FIG. 17, the reliability determiner 148 subtracts a preset number of days from the number of days in the menstrual cycle, which is calculated in the menstrual cycle method estimation process, to determine a comparison number of days (Step S81). Subsequently, the reliability determiner 148 subtracts the date of the first day of the menstrual cycle from today's date to calculate the number of elapsed days (Step S82). Then, the reliability determiner 148 determines whether the number of elapsed days is greater than or equal to the comparison number of days (Step S83). If the reliability determiner 148 determines that the number of elapsed days is not greater than or equal to the comparison number of days (NO in Step S83), the process proceeds to Step S85.

On the other hand, if the reliability determiner 148 determines that the number of elapsed days is greater than or equal to the comparison number of days (YES in Step S83), the process proceeds to Step S84. In Step S84, the reliability determiner 148 obtains the average reference body temperature determined based on the N-th degree regression equation obtained in the degree determination process. The reliability determiner 148 also determines whether all of the actual measurements after the comparison number of days has elapsed since the first day of the current menstrual cycle, among the actual measurements during the current menstrual cycle, are lower than the average reference body temperature. If the reliability determiner 148 determines that at least one of the actual measurements is not lower than the average reference body temperature (NO in Step S84), the process proceeds to Step S85. In Step S85, the reliability determiner 148 sets the reliability flag to "not low". On the other hand, if the reliability determiner 148 determines that all of the actual measurements are lower than the average reference body temperature (YES in Step S84), the process proceeds to Step S86. In Step S86, the reliability determiner 148 sets the reliability flag to "low". After Step S85 or S86, the reliability determiner 148 terminates the reliability determination process.

As described above, also according to this embodiment, decrease in estimation accuracy due to using actual measurements during the current menstrual cycle is prevented. The system controller 14 may determine the reliability, for example, by combining the reliability determination process in the fourth embodiment and the reliability determination process in the fifth embodiment.

6. Sixth Embodiment

Figure 19:
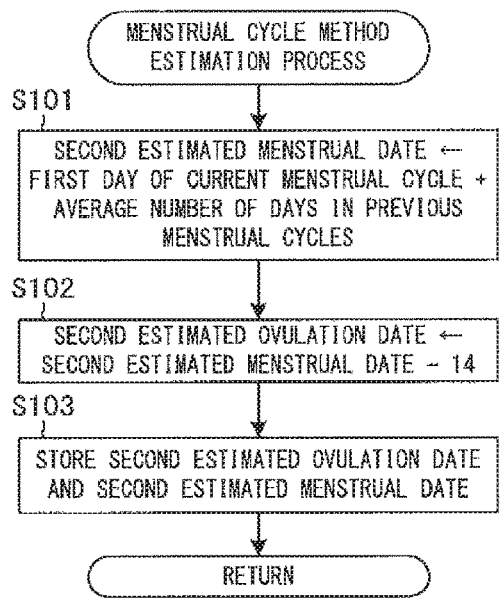
FIG. 19 is a flowchart showing an example process of the menstrual cycle method estimation process in the system controller 14 of the information processing server 1 according to an embodiment.

The following describes a sixth embodiment with reference to FIGS. 18 and 19. The configuration of the information processing system S, the configuration of the information processing server 1, and the functional blocks of the system controller 14 are the same as those in the first embodiment.

In this embodiment, the system controller 14 determines whether previous menstrual cycles were stable. If the previous menstrual cycles were stable, the system controller 14 estimates an ovulation date, based on the numbers of days in the previous menstrual cycles. Specifically, when the difference between the number of days in each of a plurality of previous menstrual cycles and the average value of the numbers of days in the plurality of previous menstrual cycles is less than or equal to a predetermined value, the estimator 143 estimates an ovulation date, based on the average value. When the menstrual cycles were stable, the system controller 14 does not need to perform the estimation by the basal body temperature method.

If the difference between the menstrual date estimated by the estimator 143 based on the average number of days in the plurality of menstrual cycles and the actual menstrual date is greater than a predetermined value, the estimator 143 may estimate an ovulation date by the basal body temperature method, without using the average number of days in the menstrual cycles. In this case, the preceding menstrual cycle is irregular. In this case, it is worth performing the estimation by the basal body temperature method.

In this embodiment, in the storage unit 12 of the information processing server 1, an estimated menstrual date DB may be further created. The estimated menstrual date DB stores an ovulation date and a menstrual date that are estimated based on the average number of days in the menstrual cycles. Specifically, the estimated menstrual date DB stores a user ID, the date of the first day of a menstrual cycle, a second estimated ovulation date, and a second estimated menstrual date in association with each other. The user ID indicates a user whose ovulation date and menstrual date were estimated. The date of the first day indicates the first day of the menstrual cycle for which the estimation process was performed. The second estimated ovulation date and the second estimated menstrual date are the ovulation date and the menstrual date that were estimated.

FIG. 18 is a flowchart showing an example process of the estimation process in the system controller 14 of the information processing server 1 according to this embodiment. In FIG. 18, the same steps as in FIG. 6 are denoted by the same reference signs. As shown in FIG. 18, if the estimator 143 determines in Step S2 that the body temperature was measured four or more times every week during the current menstrual cycle (YES in Step S2), the process proceeds to Step S91. In Step S91, the estimator 143 determines whether the second estimated ovulation date and the second estimated menstrual date that correspond to the user ID included in the estimation request and to the date of the first day of the current menstrual cycle are stored in the estimated menstrual date DB. If the estimator 143 determines that the second estimated ovulation date and the second estimated menstrual date are stored (YES in Step S91), the process proceeds to Step S92. In Step S92, the estimator 143 sends, to the user terminal 2, the second estimated ovulation date and the second estimated menstrual date that correspond to the user ID included in the request and to the date of the first day of the current menstrual cycle. The fact that the second estimated ovulation date and the second estimated menstrual date are stored means that the menstrual cycle has already met requirements for estimating an ovulation date and a menstrual date based on the average of a plurality of previous menstrual cycles. After Step S92, the estimator 143 terminates the estimation process.

On the other hand, if the estimator 143 determines that the second estimated ovulation date and the second estimated menstrual date are not stored (NO in Step S91), the process proceeds to Step S93. In Step S93, the estimator 143 determines whether the second estimated ovulation date and the second estimated menstrual date that correspond to the user ID included in the estimation request and to the date of the first day of the preceding menstrual cycle are stored in the estimated menstrual date DB. If the estimator 143 determines that the second estimated ovulation date and the second estimated menstrual date are not stored (NO in Step S93), the process proceeds to Step S95.

On the other hand, if the estimator 143 determines that the second estimated ovulation date and the second estimated menstrual date are stored (YES in Step S93), the process proceeds to Step S94. In Step S94, the estimator 143 determines whether the difference between the second estimated menstrual date corresponding to the user ID included in the estimation request and to the date of the first day of the preceding menstrual cycle and the actual menstrual date is less than or equal to a preset threshold number of days. If the reliability determiner 143 determines that the difference is not less than or equal to the threshold number of days (NO in Step S94), the process proceeds to Step S4.

On the other hand, if the estimator 143 determines that the difference is less than or equal to the threshold number of days (YES in Step S94), the process proceeds to Step S95. In Step S95, the estimator 143 determines whether there are a predetermined number of previous menstrual cycles or more, based on the menstrual dates retrieved from the menstrual date DB 12c. If the reliability determiner 143 determines that there are not the predetermined number of previous menstrual cycles or more (NO in Step S95), the process proceeds to Step S4.

On the other hand, if the reliability determiner 143 determines that there are the predetermined number of previous menstrual cycles or more (YES in Step S95), the process proceeds to Step S96. In Step S96, the estimator 143 calculates the average number of days in the plurality of previous menstrual cycles, based on the menstrual dates retrieved from the menstrual date DB 12c. Subsequently, based on the numbers of days in the plurality of previous menstrual cycles and the average number of days, the estimator 143 calculates the variance of the numbers of days in the menstrual cycles (Step S97). This variance is the magnitude of the difference between the numbers of days in the plurality of previous menstrual cycles and the average number of days. Then, the estimator 143 determines whether the calculated variance is less than or equal to a preset threshold value (Step S98). If the reliability determiner 143 determines that the variance is not less than or equal to the threshold value (NO in Step S98), the process proceeds to Step S4.

On the other hand, if the estimator 143 determines that the variance is less than or equal to the threshold value (YES in Step S98), the process proceeds to Step S99. In Step S99, the estimator 143 performs the menstrual cycle method estimation process. Subsequently, the estimator 143 sends the second estimated ovulation date and the second estimated menstrual date, which are estimated in the menstrual cycle method estimation process, to the user terminal 2 (Step S100). After Step S100, the estimator 143 terminates the estimation process.

FIG. 19 is a flowchart showing an example process of the menstrual cycle method estimation process in the system controller 14 of the information processing server 1 according to this embodiment. As shown in FIG. 19, the estimator 143 adds the calculated average number of days in the menstrual cycles calculated in the estimation process to the date of the first day of the current menstrual cycle to calculate a second estimated menstrual date (Step S101). Subsequently, the estimator 143 subtracts fourteen days from the second estimated menstrual date to calculate a second estimated ovulation date (Step S102). Then, the estimator 143 stores the second estimated ovulation date and the second estimated menstrual date in the estimated menstrual date DB, in association with the user ID included in the estimation request and with the date of the first day of the current menstrual cycle (Step S103). After Step S103, the estimator 143 terminates the menstrual cycle method estimation process.

As described above, according to this embodiment, when the difference between each of a plurality of previous menstrual cycles and the average of the plurality of menstrual cycles is less than or equal to a predetermined value, the system controller 14 estimates an ovulation date and the next menstrual date based on the average of the plurality of menstrual cycles, without using either a low-temperature-phase reference body temperature or a low-temperature-phase reference body temperature. Thus, when the previous menstrual cycles were stable, the information processing server 1 improves estimation accuracy, even without using the regression equation of a function that approximates the relationship between body temperature data and dates.

When the difference between the menstrual date estimated based on the average of the plurality of menstrual cycles and the actual menstrual date is greater than a predetermined value, the system controller 14 may estimate an ovulation date in the current menstrual cycle, based on a low-temperature-phase reference body temperature and a high-temperature-phase reference body temperature that are determined by using the regression equation of a function that approximates actual measurements during at least one previous menstrual cycle and actual measurements during the current menstrual cycle. When the preceding menstrual cycle was irregular, this prevents decrease in estimation accuracy due to using the average of previous menstrual cycles.

The system controller 14 may determine whether to estimate an ovulation date by the basal body temperature method, for example, by combining at least one of the reliability determination processes in the fourth and fifth embodiments with the determination process in this embodiment.

7. Seventh Embodiment

Figure 20:
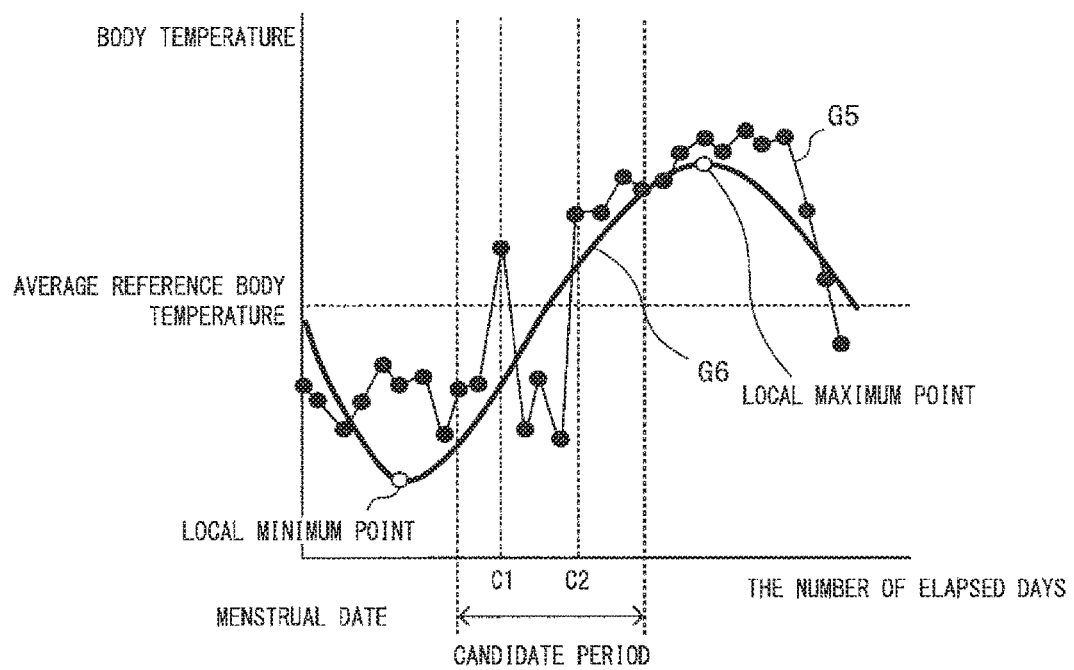
FIG. 20 is a diagram showing an example relationship between a graph of changes in body temperature data, a curve graph that approximates the graph of the changes, and candidates for a reference date.

The following describes a seventh embodiment with reference to FIGS. 20 and 21. The configuration of the information processing system S, the configuration of the information processing server 1, and the functional blocks of the system controller 14 are the same as those in the first embodiment.

A reference date is defined as a date on which the body temperature data becomes higher than a determination reference body temperature. Thus, for any reason, there may be a plurality of candidates for the reference date. FIG. 20 is a diagram showing an example relationship between a graph of changes in body temperature data, a curve graph that approximates the graph of the changes, and candidates for a reference date. For example, in FIG. 20, the graph G5 shows changes in body temperature data, and the graph G6 is a curve graph that approximates the graph G5. As shown in the Graph G5, the date that is C1 days after a menstrual date and the date that is C2 days after the menstrual date are each a candidate for the reference date. In this embodiment, when there are a plurality of candidates for the reference date, the system controller 14 determines one of the plurality of candidates to be the reference date, based on a predetermined criterion. A candidate for the reference date is referred to as a candidate reference date. At this time, the system controller 14 selects candidate reference dates from the period from a predetermined number of days after (e.g., three days after) the date corresponding to a local minimum point on the curve graph to a predetermined number of days before (e.g., three days before) the date corresponding to a local maximum point on the curve graph. The reason is, for example, that the transition from a low-temperature phase to a high-temperature phase is less likely to occur between the date corresponding to the local minimum point and the predetermined number of days after then, and between the date corresponding to the local maximum point and the predetermined number of days before then. The period from which candidate reference dates are selected is referred to as a candidate period.

As the predetermined criterion, various criteria are possible. For example, the system controller 14 may determine the latest of a plurality of candidate reference dates to be the reference date. In this case, a date on which the body temperature exceeded the determination reference body temperature because of a fever during the low-temperature phase is excluded from the reference date. In the example of FIG. 20, the day that is C2 days after the menstrual date is determined to be the reference date.

Alternatively, the system controller 14 may determine the earliest of the candidate reference dates that meet the following criterion to be the reference date. The criterion is both that all the body temperature data for a predetermined number of consecutive days (e.g., two days) starting forward from the day after a candidate reference date are higher than the determination reference body temperature, and that all the body temperature data for a predetermined number of consecutive days (e.g., two days) starting backward from two days before the candidate reference date are lower than the determination reference body temperature. The consecutive days may be, for example, consecutive days according to the calendar or consecutive days in ascending order of dates on which measurement data was obtained. In this case, a date on which the body temperature exceeded the determination reference body temperature because of a fever during the low-temperature phase is excluded from the reference date. A date on which the body temperature exceeded the determination reference body temperature after the body temperature became lower than the determination reference body temperature, for example, because of an error in measurement during the high-temperature phase is also excluded from the reference date. In the example of FIG. 20, the day that is C2 days after the menstrual date is determined to be the reference date.

FIG. 21 is a flowchart showing an example process of the basal body temperature method estimation process in the system controller 14 of the information processing server 1 according to this embodiment. In FIG. 21, the same steps as in FIG. 8 are denoted by the same reference signs. As shown in FIG. 21, after Steps S11 to S16, the estimator 143 determines a candidate period (Step S111). Specifically, the estimator 143 adds a certain number of days prestored in the storage unit 12 to the date corresponding to the local minimum point to calculate the first day of the candidate period. The estimator 143 also subtracts a certain number of days prestored in the storage unit 12 from the date corresponding to the local maximum point to calculate the last day of the candidate period. Subsequently, the estimator 143 identifies candidate reference date(s) on which the body temperature data becomes higher than the average reference body temperature, within the candidate period (Step S112). Specifically, the estimator 143 performs the following process using each of the dates included in the candidate period as a date of interest. The estimator 143 identifies, as candidate reference dates, all the dates of interest on which the body temperature data is higher than the average reference body temperature and whose preceding day's body temperature data is lower than the average reference body temperature.

Then, the estimator 143 determines whether the number of the identified candidate reference dates is greater than one (Step S113). If the estimator 143 determines that the number of the identified candidate reference dates is not greater than one (NO in Step S113), the process proceeds to Step S114. In Step S114, the estimator 143 determines the identified candidate reference date to be a reference date (Step S114). After that, the estimator 143 performs Steps S18 and S19.

On the other hand, if the estimator 143 determines that the number of the identified candidate reference dates is greater than one (YES in Step S113), the process proceeds to Step S115. In Step S115, the estimator 143 determines a reference date from among the plurality of candidate reference dates, based on the predetermined criterion. For example, the estimator 143 determines the latest of the plurality of candidate reference dates to be the reference date. Alternatively, for example, the estimator 143 performs the following determination in ascending order of the candidate reference dates. Specifically, the estimator 143 determines whether all the body temperature data between the day after a candidate reference date and a certain number of days, prestored in the storage unit 12, after then are higher than the average reference body temperature. If all the body temperature data are higher than the average reference body temperature, the estimator 143 determines whether all the body temperature data between two days before the candidate reference date and a certain number of days, prestored in the storage unit 12, before then are lower than the average reference body temperature. The estimator 143 determines the candidate reference date for which all the body temperature data are first determined to be lower than the average reference body temperature to be the reference date. After determining the reference date, the estimator 143 performs Steps S18 and S19.

As described above, according to this embodiment, when there are a plurality of candidate reference dates during the candidate period from a predetermined number of days after the date corresponding to a local minimum value to a predetermined number of days before the date corresponding to a local maximum value, one of the candidate reference dates is determined to be a reference date, based on a predetermined criterion. Thus, a reference date is properly identified even if measurement data includes any noise. Consequently, estimation accuracy is improved.

In the third to sixth embodiments, the system controller 14 may estimate an ovulation date, based on a date on which the body temperature calculated by using the regression equation becomes higher than the average of the low-temperature-phase reference body temperature and the high-temperature-phase reference body temperature. In the third to seventh embodiments, the system controller 14 may calculate a weighted average of each actual measurement during previous menstrual cycle(s) and the corresponding actual measurement during the current menstrual cycle, and obtain the regression equation of a curve graph that approximates the a graph of changes including the weighted averages.

In the embodiments described above, an information processing device according to the present invention is a server device in a client-server system. However, the information processing device according to the present invention may be an information processing device other than the server device. For example, the information processing device according to the present invention may be the user terminal 2. The information processing device may obtain actual measurements of a user who uses the information processing device and estimate an ovulation date of the user.

REFERENCE SIGNS LIST 1 information processing server
2 user terminal
11 communication unit
12 storage unit
12a member information DB
12b body temperature DB
12c menstrual date DB
13 input/output interface
14 system controller
14a CPU
14b ROM
14c RAM
15 system bus
141 regression equation obtainer
142 reference body temperature determiner
143 estimator
144 second regression equation obtainer
145 second reference body temperature determiner
146 second estimator
147 degree determiner
148 reliability determiner
NW network
S information processing system

The invention claimed is:

1. An information processing device comprising:
at least one memory configured to store computer program code;
at least one processor configured to access said at least one memory and operate as instructed by said computer program code, said computer program code including:
obtaining code configured to cause at least one of said at least one processor to obtain an equation of a function of date, the function approximating a relationship between dates and body temperatures with a local minimum value and a local maximum value, the body temperatures being obtained based on actual measurements during at least one menstrual cycle;
determining code configured to cause at least one of said at least one processor to determine a low-temperature-phase reference body temperature, based on a first group of body temperatures of a first group of days identified based on a date corresponding to the local minimum value in the function defined by the obtained equation, and determine a high temperature-phase reference body temperature, based on a second group of body temperatures of a second group of days identified based on a date corresponding to the local maximum value in the function defined by the obtained equation;
estimating code configured to cause at least one of said at least one processor to accurately estimate an ovulation date in a current menstrual cycle, based on a determination reference body temperature set at a value between the determined low-temperature-phase reference body temperature and the determined high-temperature-phase reference body temperature and on measurement data including the body temperatures and dates associated with the body temperatures; and
sending code configured to cause at least one of said at least one processor to send the accurately-estimated ovulation date to a user terminal.

2. The information processing device according to claim 1, wherein the estimating code is configured to cause at least one of said at least one processor to identify a date on which a body temperature becomes higher than the determination reference body temperature as a reference date, among the dates included in the measurement data, and accurately estimate the ovulation date, based on the reference date.

3. The information processing device according to claim 1, wherein when there are a plurality of candidate dates on which a body temperature is higher than the determination reference body temperature and whose preceding day's body temperature is lower than the determination reference body temperature, during a period from a predetermined number of days after the date corresponding to the local minimum value to a predetermined number of days before the date corresponding to the local maximum value, the estimating code causes at least one of said at least one processor to determine one of the plurality of candidate dates to be a reference date, based on a predetermined criterion, and accurately estimate the ovulation date, based on the reference date.

4. The information processing device according to claim 1, wherein the estimating code is configured to cause at least one of said at least one processor to identify a date on which body temperature calculated by using the obtained equation becomes higher than the determination reference body temperature as a reference date, and accurately estimate the ovulation date, based on the reference date.

5. The information processing device according to claim 1, wherein the body temperatures are obtained based on actual measurements during at least one previous menstrual cycle and on actual measurements during the current menstrual cycle.

6. The information processing device according to claim 5, wherein the obtaining code is configured to cause at least one of said at least one processor to assign a higher weight to the actual measurements during the current menstrual cycle than to the actual measurements during the at least one previous menstrual cycle, calculate a weighted average of each actual measurement during the at least one previous menstrual cycle and a corresponding actual measurement during the current menstrual cycle, and obtain the equation of the function that approximates a relationship between the weighted averages and dates.

7. The information processing device according to claim 1, further comprising:
second obtaining code configured to cause at least one of said at least one processor to obtain a plurality of equations of mutually different degrees of a plurality of functions, each function approximating a relationship between dates and body temperatures with a local minimum value and a local maximum value, the body temperatures being obtained based on actual measurements during at least one previous menstrual cycle;
second determining code configured to cause at least one of said at least one processor to determine a low-temperature-phase reference body temperature, based on a third group of measurements of a third group of days identified based on a date corresponding to the local minimum value in the function defined by the equation obtained by the second obtaining code, and determine a high-temperature-phase reference body temperature, based on a fourth group of measurements of a fourth group of days identified based on a date corresponding to the local maximum value in the function defined by the equation obtained by the second obtaining code, for each of the equations obtained by the second obtaining code;
second estimating code configured to cause at least one of said at least one processor to estimate a menstrual date in the at least one previous menstrual cycle, based on a body temperature set at a value between the low-temperature-phase reference body temperature and the high-temperature-phase reference body temperature that are determined by the second determining code and on the actual measurements, for each of the equations obtained by the second obtaining code; and
identifying code configured to cause at least one of said at least one processor to identify a degree of an equation that minimizes a difference between a menstrual date estimated by the second estimating code and an actual menstrual date, from among the plurality of equations obtained by the second obtaining code,
wherein the obtaining code causes at least one of said at least one processor to obtain the equation of the degree identified by the identifying code.

8. The information processing device according to claim 1, wherein the body temperatures are obtained based on actual measurements during at least one previous menstrual cycle and on actual measurements during the current menstrual cycle,
the information processing device further comprises determination code configured to cause at least one of said at least one processor to determine whether a reliability of the actual measurements during the current menstrual cycle meets a predetermined requirement, based on the actual measurements during the at least one previous menstrual cycle, and
if the determination code causes at least one of said at least one processor to determine that the reliability does not meet the predetermined requirement, the estimating code causes at least one of said at least one processor to accurately estimate the ovulation date based on information about the at least one previous menstrual cycle, without using either the low-temperature-phase reference body temperature or the high-temperature-phase reference body temperature that is determined based on the actual measurements during the current menstrual cycle.

9. The information processing device according to claim 1, wherein when a difference between a plurality of previous menstrual cycles and an average of the plurality of menstrual cycles is less than or equal to a predetermined value, the estimating code causes at least one of said at least one processor to accurately estimate the ovulation date and a next menstrual date based on the average of the plurality of menstrual cycles, without using either the low-temperature-phase reference body temperature or the low-temperature-phase reference body temperature.

10. The information processing device according to claim 9, wherein when a difference between a menstrual date estimated based on the average of the plurality of menstrual cycles and an actual menstrual date is greater than a predetermined value, the estimating code causes at least one of said at least one processor to accurately estimate an ovulation date in the current menstrual cycle, based on the low-temperature-phase reference body temperature and the high-temperature-phase reference body temperature that are determined by using the equation of the function that approximates a relationship between the body temperatures and the dates, the body temperatures being obtained based on actual measurements during at least one previous menstrual cycle and actual measurements during the current menstrual cycle.

11. An information processing method performed by an information processing device comprising at least one memory configured to store computer program code, and at least one processor configured to access said at least one memory and operate as instructed by said computer program code to perform the information processing method, the information processing method comprising:
obtaining an equation of a function of date, the function approximating a relationship between dates and body temperatures with a local minimum value and a local maximum value, the body temperatures being obtained based on actual measurements during at least one menstrual cycle;
determining a low-temperature-phase reference body temperature, based on a first group of body temperatures of a first group of days identified based on a date corresponding to the local minimum value in the function defined by the obtained equation;
determining a high-temperature-phase reference body temperature, based on a second group of body temperatures of a second group of days identified based on a date corresponding to the local maximum value in the function defined by the obtained equation;
accurately estimating an ovulation date in a current menstrual cycle, based on a determination reference body temperature set at a value between the determined low-temperature-phase reference body temperature and the determined high-temperature-phase reference body temperature and on measurement data including the body temperatures and dates associated with the body temperatures; and sending the accurately-estimated ovulation date to a user terminal.

12. A non-transitory computer-readable medium storing a computer program code, the computer program code causing an information processing device comprising at least one processor to access said non-transitory computer-readable medium and operate as instructed by said computer program code to:

obtain an equation of a function of date, the function approximating a relationship between dates and body temperatures with a local minimum value and a local maximum value, the body temperatures being obtained based on actual measurements during at least one menstrual cycle;

determine a low-temperature-phase reference body temperature, based on a first group of body temperatures of a first group of days identified based on a date corresponding to the local minimum value in the function defined by the obtained equation;

determine a high temperature-phase reference body temperature, based on a second group of body temperatures of a second group of days identified based on a date corresponding to the local maximum value in the function defined by the obtained equation;

accurately estimate an ovulation date in a current menstrual cycle, based on a determination reference body temperature set at a value between the determined low-temperature-phase reference body temperature and the determined high-temperature-phase reference body temperature and on measurement data including the body temperatures and dates associated with the body temperatures; and send the accurately-estimated ovulation date to a user terminal.

* * * * *